(12) United States Patent
Chen et al.

(10) Patent No.: US 10,755,129 B2
(45) Date of Patent: Aug. 25, 2020

(54) DISEASE RECOGNITION FROM IMAGES HAVING A LARGE FIELD OF VIEW

(71) Applicant: The Climate Corporation, San Francisco, CA (US)

(72) Inventors: Yaqi Chen, Chesterfield, MO (US); Wei Guan, Pleasanton, CA (US)

(73) Assignee: THE CLIMATE CORPORATION, San Francisco, CA (US)

( * ) Notice: Subject to any disclaimer, the term of this patent is extended or adjusted under 35 U.S.C. 154(b) by 0 days.

(21) Appl. No.: 16/554,485

(22) Filed: Aug. 28, 2019

(65) Prior Publication Data

US 2019/0384998 A1   Dec. 19, 2019

Related U.S. Application Data

(63) Continuation of application No. 15/725,284, filed on Oct. 5, 2017, now Pat. No. 10,423,850.

(51) Int. Cl.
*G06K 9/32* (2006.01)
*C12N 15/82* (2006.01)
(Continued)

(52) U.S. Cl.
CPC ............. *G06K 9/3241* (2013.01); *A01H 1/04* (2013.01); *C12N 15/8281* (2013.01);
(Continued)

(58) Field of Classification Search
CPC ...... G06K 9/3241; G06K 9/34; G06K 9/4652; G06K 9/68; G06K 9/00664; G06K 9/4642; G06K 9/6271; C12N 15/8281; A01H 1/04
(Continued)

(56) References Cited

U.S. PATENT DOCUMENTS 6,654,506 B1   11/2003   Luo et al.
6,837,617 B1   1/2005   Koltunov
(Continued)

FOREIGN PATENT DOCUMENTS

WO   WO2013/101547 A1   7/2013
WO   WO 2014/018427 A2   1/2014
(Continued)

OTHER PUBLICATIONS

The International Bureau of WIPO, "International Preliminary Report on Patentability" in application No. PCT/US2018/048169, dated Mar. 3, 2020, 9 pages.
(Continued)

*Primary Examiner* — Thomas K Pham
*Assistant Examiner* — Mitchell T Oestreich
(74) *Attorney, Agent, or Firm* — Hickman Palermo Becker Bingham LLP

(57) ABSTRACT

In an embodiment, a computer-implemented method of detecting infected objects from large field-of-view images is disclosed. The method comprises receiving, by a processor, a digital image capturing multiple objects; generating, by the processor, a plurality of scaled images from the digital image respectfully corresponding to a plurality of scales; and computing a group of feature matrices for the digital image. The method further comprises, for each of the plurality of scaled images. selecting a list of candidate regions from the scaled image each likely to capture a single object; and for each of the list of candidate regions, performing the following steps: mapping the candidate region back to the digital image to obtain a mapped region; identifying a corresponding portion from each of the group of feature matrices based on the mapping; and determining whether the candidate region is likely to capture the single object infected with a disease based on the group of corresponding portions. In
(Continued)

addition, the method comprises choosing a group of final regions from the lists of mapped regions based on the determining; and causing display of information regarding the group of final regions.

20 Claims, 13 Drawing Sheets

(51) Int. Cl.
    *G06K 9/46*         (2006.01)
    *G06K 9/62*         (2006.01)
    *G06K 9/00*         (2006.01)
    *A01H 1/04*        (2006.01)
    *G06K 9/68*         (2006.01)
    *G06K 9/34*         (2006.01)

(52) U.S. Cl.
    CPC ....... *G06K 9/00664* (2013.01); *G06K 9/4642* (2013.01); *G06K 9/6271* (2013.01); *G06K 9/34* (2013.01); *G06K 9/4652* (2013.01); *G06K 9/68* (2013.01)

(58) Field of Classification Search
    USPC .......................................................... 359/631
    See application file for complete search history.

(56) References Cited

U.S. PATENT DOCUMENTS

| | | |
|---|---|---|
| 2004/0001636 A1 | 1/2004 | Micel et al. |
| 2004/0146615 A1 | 7/2004 | McDonald |
| 2010/0132023 A1 | 5/2010 | Reese et al. |
| 2012/0114187 A1 | 5/2012 | Duarte |
| 2013/0070126 A1 | 3/2013 | Albu |
| 2013/0136312 A1 | 5/2013 | Tseng et al. |
| 2014/0009600 A1 | 1/2014 | Ibamoto |
| 2014/0023243 A1 | 1/2014 | Nagaraj |
| 2014/0035752 A1 | 2/2014 | Johnson |
| 2014/0301607 A1 | 10/2014 | Anderson |
| 2015/0187109 A1 | 7/2015 | Mentzer |
| 2015/0206255 A1 | 7/2015 | Groeneveld |
| 2016/0000020 A1 | 1/2016 | Sugimoto |
| 2016/0021891 A1 | 1/2016 | Von Maltzahn |
| 2016/0148104 A1 | 5/2016 | Itzhaky et al. |
| 2016/0223506 A1 | 8/2016 | Shriver |
| 2016/0225135 A1 | 8/2016 | Young |
| 2016/0239709 A1 | 8/2016 | Shriver |
| 2016/0253595 A1 | 9/2016 | Mathur et al. |
| 2016/0300363 A1 | 10/2016 | Young |
| 2016/0309646 A1 | 10/2016 | Starr |
| 2017/0206415 A1 | 7/2017 | Redden |
| 2017/0223947 A1* | 8/2017 | Gall ................... A01M 7/0089 |
| 2017/0374323 A1 | 12/2017 | Gornik |
| 2018/0259496 A1 | 9/2018 | McPeek |
| 2019/0066234 A1 | 2/2019 | Bedoya |
| 2019/0108413 A1 | 4/2019 | Chen |
| 2020/0051180 A1 | 2/2020 | Bedoya |

FOREIGN PATENT DOCUMENTS

| | | |
|---|---|---|
| WO | WO 2016/025848 A1 | 2/2016 |
| WO | WO2017/078886 A1 | 5/2017 |

OTHER PUBLICATIONS

Current Claims in applicaiton No. PCT/US2018/048169, dated Mar. 2020, 4 pages.
Chen, U.S. Appl. No. 15/725,284, filed Oct. 5, 2017, Notice of Allowance, dated May 15, 2019.
Bedoya, U.S. Appl. No. 15/688,567, filed Aug. 28, 2017, Office Action, dated Nov. 16, 2018.
Bedoya, U.S. Appl. No. 15/688,567, filed Aug. 28, 2017, Notice of Allowance, dated Aug. 8, 2019.
Bedoya, U.S. Appl. No. 15/688,567, filed Aug. 28, 2017, Interview Summary, dated Feb. 14, 2019.
Bedoya, U.S. Appl. No. 15/688,567, filed Aug. 28, 2017, Final Office Action, dated May 31, 2019.
Bedoya, U.S. Appl. No. 15/688,567, filed Aug. 28, 2017, Advisory Action, dated Aug. 5, 2019.
M. Arjovsky and L. Bottou. "Towards Principled Methods for Training Generative Adversarial Networks", CoRR, abs/1701.04862, dated 2017, 41 pages.
Current Claims in application No. PCT/US2018/054348 dated Dec. 2018, 5 pages.
Gavhale et al., "An Overiew of the Research on Plant Leaves Disease Detection Using Image Processing Techiques", IOSR Journal of Computer Engineering, vol. 16, Issue 1, dated Janaury 2014, 7 pages.
Girshick et al., "Rich Feature Hierarchies for Accurate Object Detection and Semantic Segmentation",Proceedings of the 2014 IEEE Conference on Computer Vision and Pattern Recognition, 2014, 21pages.
H. A. Rowley, S. Baluja, and T. Kanade. "Neural Network-based Face Detection". IEEE Trans. Pattern Anal. Mach. Intell., 20(1):23-38, dated Jan. 1998. ISSN 0162-8828, 6 pages.
I. Gulrajani, F. Ahmed, M. Arjovsky, V. Dumoulin, and A. C. Courville. Improved training of wasserstein gans. CoRR, abs/1704.00028, dated 2017, 19 pages.
I. J. Goodfellow, J. Pouget-Abadie, M. Mirza, B. Xu, D. Warde-Farley, S. Ozair, A. Courville, and Y. Bengio. "Generative Adversarial Networks". ArXiv e-prints, Jun. 2014, 9 pages.
International Searching Authority, "Search Report" in application No. PCT/US2018/048169, dated Dec. 10, 2018, 19 pages.
J. Hoffman, S. Guadarrama, E. Tzeng, J. Donahue, R. B. Girshick,T. Darrell, and K. Saenko. "LSDA: Large Scale Detection Through Adaptation". CoRR, abs/1407.5035, dated 2014, 9 pages.
J. Hosang, R. Benenson, and B. Schiele. "How Good are Detection Proposals, Really?" In BMVC, dated 2014, 25 pages.
J. R. R. Uijlings, K. E. A. van de Sande, T. Gevers, and A. W. M. Smeulders. "Selective Search for Object Recognition", International Journal of Computer Vision, dated 2013, 14 pages.
J. Redmon, S. K. Divvala, R. B. Girshick, and A. Farhadi. "You Only Look Once: Unified, Real-time Object Detection". CoRR, abs/1506.02640, dated 2015, 10 pages.
Current Claims in application No. PCT/US2018/048169, dated Dec. 2018, 3 pages.
L. Z. Piotr Dollar. "Structured Forests for Fast Edge Detection". In ICCV, Dec. 2013, 8 pages.
Valliammal et al., "A Novel Approach for Planet Leaf Image Segmentation Using Fuzzy Clustering", International Journal of Computer Applications, dated Oct. 20, 2012, 11 pages.
M. Arjovsky, S. Chintala, and L. Bottou. "Wasserstein GAN". CoRR, abs/1701.07875, dated 2017, 32 pages.
Montes et al., "Practical Computer Vision: Theeory and Applications", Basque Center for Applied Mathematics dated 2015, 61 pages.
N. Dalai and B. Triggs. "Histograms of Oriented Gradients for Human Detection", In 2005 IEEE, Computer Society Conference on Computer Vision and Pattern Recognition, Jun. 1, 2005, 8 pages.
P. D. Larry Zitnick. "Edge Boxes: Locating Object Proposals From Edges". In ECCV. European Conference on Computer Vision, dated Sep. 2014,15 pages.
P. Dollár and C. L. Zitnick. "Fast Edge Detection Using Structured Forests", IEEE Trans. Pattern Anal. Mach. Intell., 37(8):1558-1570, 2015, 13 pages.
P. Sermanet, D. Eigen, X. Zhang, M. Mathieu, R. Fergus, and Y. Le-Cun. "Overfeat: Integrated Recognition, Localization and Detection Using Convolutional Networks". CoRR, dated 2013, 26 pages.
R. Girshick. "Fast R-CNN", In Proceedings of the International Conference on Computer Vision (ICCV), dated 2015, 9 pages.
R. Rothe, M. Guillaumin, and L. V. Gool. "Non-maximum Suppression for Object Detection by Passing Messages Between Windows.", In Asian Conference on Computer Vision (ACCV), Nov. 2014, 16 pages.

(56) References Cited

OTHER PUBLICATIONS

Ren et al., "Faster r-cnn: Towards realtime object detection with region proposal networks", Advances in Neural Information Processing Systems 28, pp. 91-99. Curran Associates, Inc., dated 2015.
T. Salimans, I. J. Goodfellow, W. Zaremba, V. Cheung, A. Radford, and X. Chen. "Improved Techniques for Training Gans". CoRR, abs/1606.03498, dated 2016, 10 pages.
The International Searching Authority, "Search Report" in application No. PCT/US2018/054348 dated Dec. 7, 2018, 11 pages.
K. He, X. Zhang, S. Ren, and J. Sun. Spatial pyramid pooling in deep convolutional networks for visual recognition. CoRR, abs/1406.4729, dated 2014, 14 pages.
Canadian Patent Office, "Search Report" in application No. 3,074,217, dated May 25, 2020, 5 pages.
Canadian Claims in application No. 3,074,217, dated May 2020, 5 pages.

* cited by examiner

Fig. 2
(a)
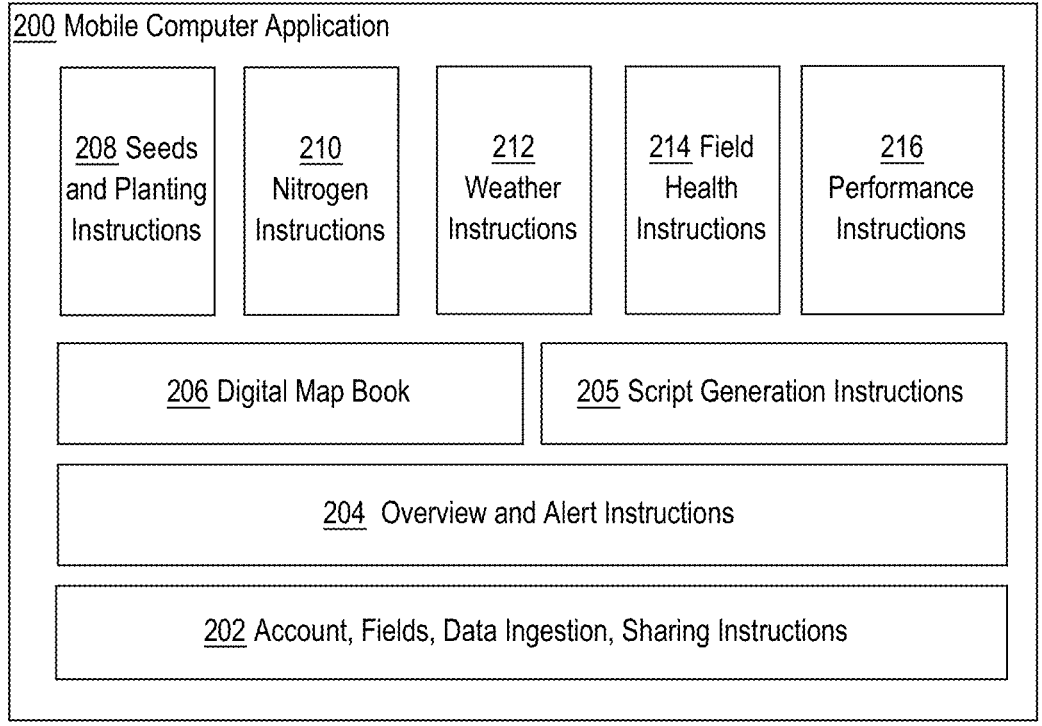
(b)
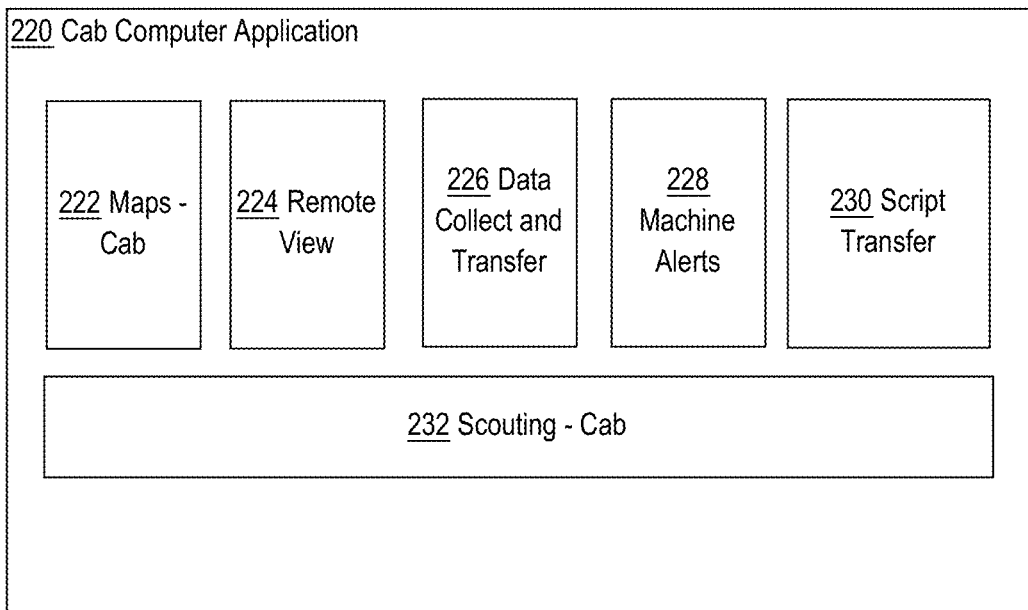

Data Manager

| Planting 1(4 Fields) | Planting 2(0 Fields) | Planting 3(0 Fields) | Planting 4(1 Fields) | | Add New Planting Plan |
|---|---|---|---|---|---|
| Crop Corn Product | Crop Corn Product | Crop Corn Product | Crop Corn Product | | |
| Plant Date: 2016-04-12 | Plant Date: 2016-04-15 | Plant Date: 2016-04-13 | Plant Date: 2016-04-13 | | |
| ILU 112 \| Pop: 34000 | ILU 83 \| Pop: 34000 | ILU 83 \| Pop: 34000 | ILU 112 \| Pop: 34000 | | |
| [Edit] [Apply] | [Edit] [Apply] | [Edit] [Apply] | [Edit] [Apply] | | + |

[Nitrogen] [Planting] [Practices] [Soil]

| | CROP | PLANTED ACRES | PRODUCT | RELATIVE MATURITY | TARGET YIELD | POPULATION(AVG) | PLA |
|---|---|---|---|---|---|---|---|
| ☐ Select All | | | | | | | |
| ☐ Ames, IA 1<br>Corn \| 100 \| Boone, IA | Corn | — | DMC82-M | 112 | 160 | 34000 | Apr |
| ☐ Austin, MN 1<br>Corn \| 100 \| Fredricks, MN | Corn | — | DMC82-M | 114 | 160 | 36000 | Apr |
| ☐ Boone, IN 1<br>Corn \| 100 \| Boone, IA | Corn | — | DMC82-M | 112 | 150 | 34000 | Apr |
| ☐ Champaign 1<br>Corn \| 100 \| Champaign, IL | Corn | — | — | 112 | 200 | 34000 | Apr |
| ☐ E Nebraska 1<br>Corn \| 100 \| Burt, NE | Corn | — | — | 112 | 160 | 34000 | Apr |

*FIG. 6*

Fig. 7
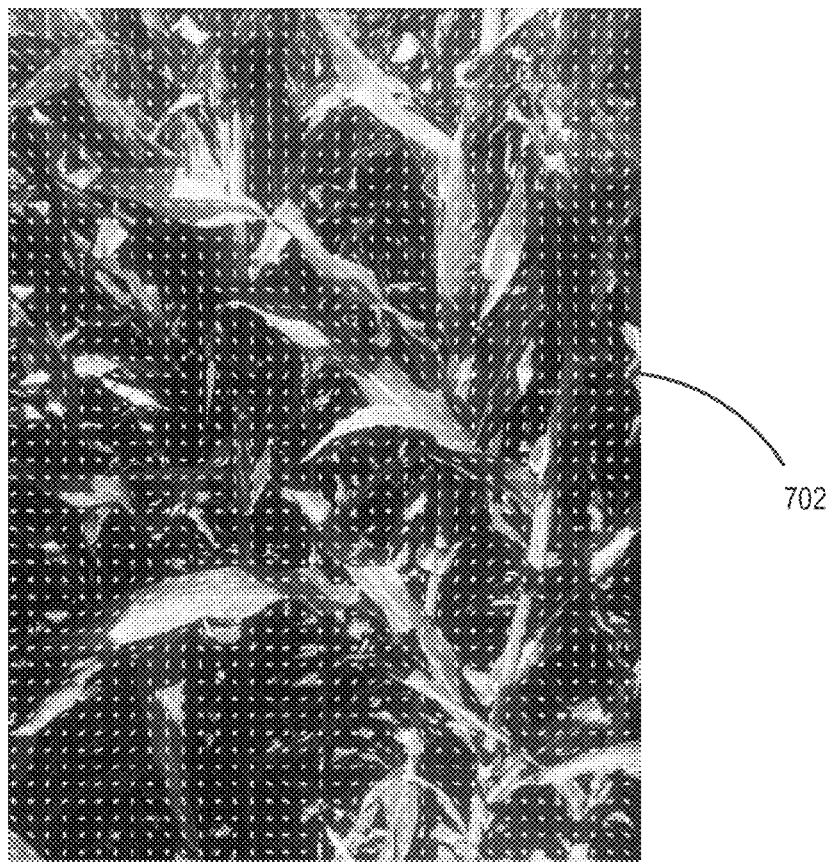
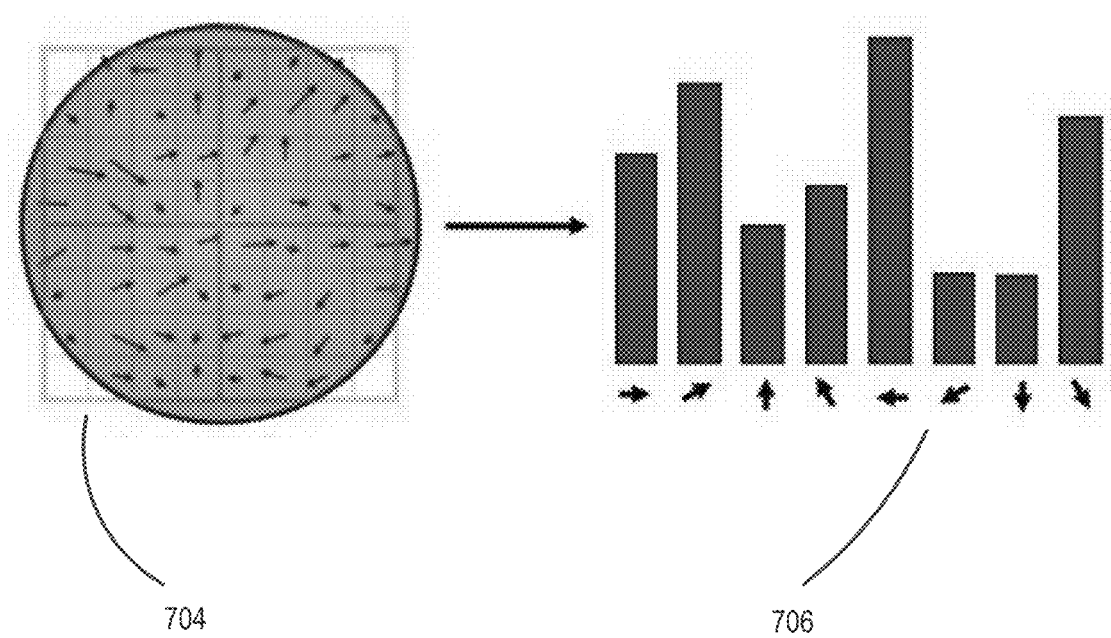

DISEASE RECOGNITION FROM IMAGES HAVING A LARGE FIELD OF VIEW

CROSS REFERENCE TO RELATED APPLICATIONS; BENEFIT CLAIM

This application claims the benefit as a Continuation of application Ser. No. 15/725,284, filed Oct. 5, 2017, the entire contents of which is hereby incorporated by reference as if fully set forth herein, under 35 U.S.C. § 120. The applicant hereby rescind any disclaimer of claim scope in the parent application or the prosecution history thereof and advise the USPTO that the claims in this application may be broader than any claim in the parent application.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright or rights whatsoever. © 2015-2017 The Climate Corporation.

FIELD OF THE DISCLOSURE

The present disclosure provides improvements in the technical fields of digital image processing and machine vision. The disclosure generally relates to detection of crop diseases using digital images, and relates more specifically to crop disease recognition from digital images having a large field of view.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Crop diseases are major concerns for farmers, as crop diseases can cause yield reduction and economic loss. Automated disease recognition and treatment can start with capturing digital images of field crops. Many machine-captured images have a large field of view ("FoV"), such as aerial scouting photos taken at a distance from a field. In such an image, disease symptoms on an individual crop may constitute a minor feature of the image, which can often go undetected with traditional image processing methods. It would be helpful to be able to quickly and accurately identify disease symptoms from large FoV images.

SUMMARY

The appended claims may serve as a summary of the disclosure.

BRIEF DESCRIPTION OF THE DRAWINGS

In the drawings:

FIG. 2 illustrates two views of an example logical organization of sets of instructions in main memory when an example mobile application is loaded for execution.

FIG. 6 depicts an example embodiment of a spreadsheet view for data entry.

FIG. 7 illustrates an example computation of histograms of oriented gradient feature vectors for regions of a large FoV image.

DETAILED DESCRIPTION

Figure 1:
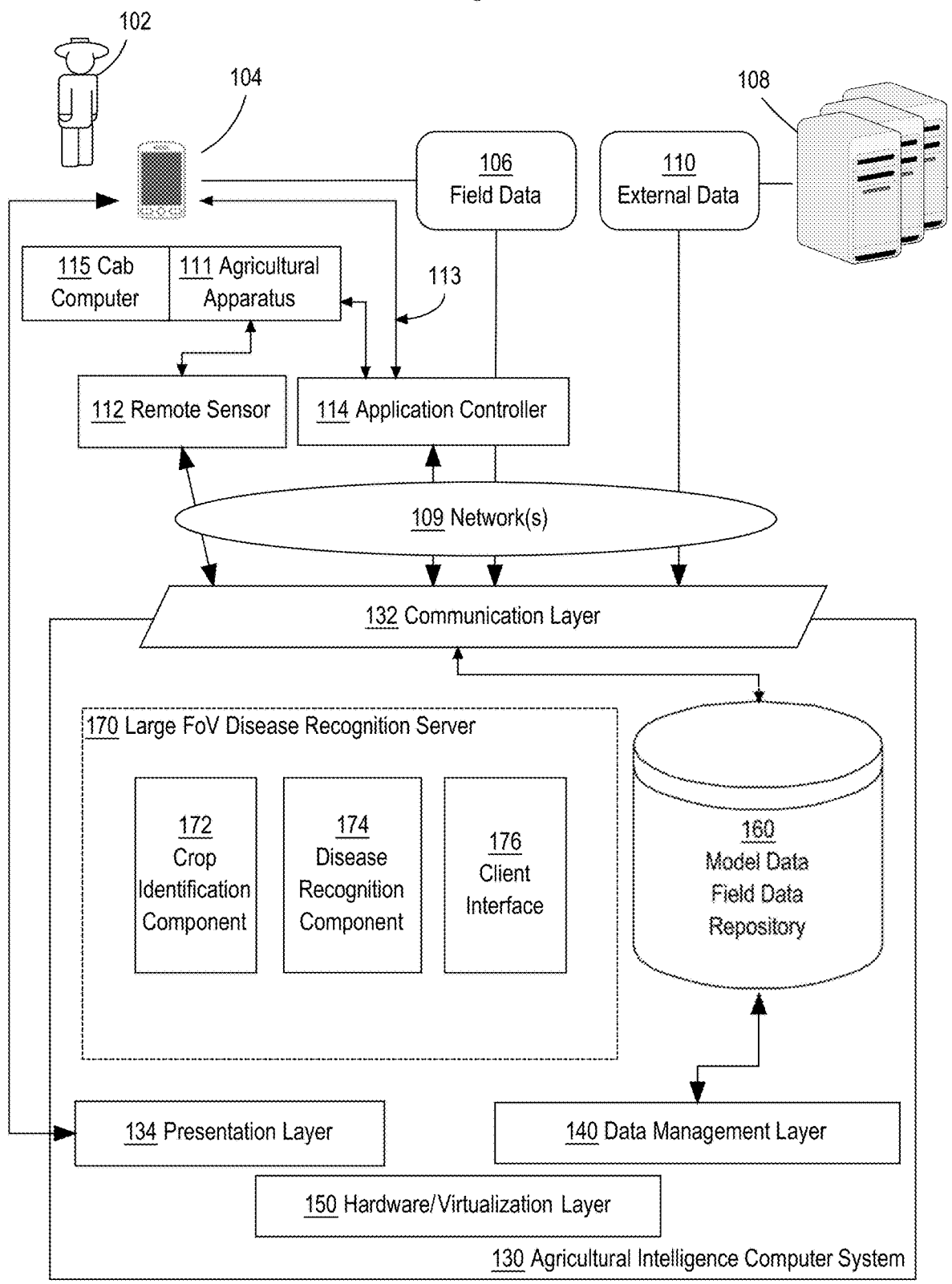
FIG. 1 illustrates an example computer system that is configured to perform the functions described herein, shown in a field environment with other apparatus with which the system may interoperate.

In the following description, for the purposes of explanation, numerous specific details are set forth in order to provide a thorough understanding of the present disclosure. It will be apparent, however, that embodiments may be practiced without these specific details. In other instances, well-known structures and devices are shown in block diagram form in order to avoid unnecessarily obscuring the present disclosure. Embodiments are disclosed in sections according to the following outline:

1. GENERAL OVERVIEW
    2. EXAMPLE AGRICULTURAL INTELLIGENCE COMPUTER SYSTEM
      2.1. STRUCTURAL OVERVIEW
      2.2. APPLICATION PROGRAM OVERVIEW
      2.3. DATA INGEST TO THE COMPUTER SYSTEM
      2.4. PROCESS OVERVIEW—AGRONOMIC MODEL TRAINING
      2.5. IMPLEMENTATION EXAMPLE—HARDWARE OVERVIEW
    3 FUNCTIONAL DESCRIPTION
    3.1 MODEL DEVELOPMENT
    3.2 IMAGE SCALING AND REGION SELECTION
    3.3 IMAGE FEATURE COMPUTATION
    3.4 IMAGE REGION CLASSIFICATION AND MAPPING
    3.5 EXAMPLE PROGRAMMABLE PROCESSES

1. General Overview

A computer system and related computer-implemented methods for recognizing crop diseases from large FoV images are disclosed. In some embodiments, the computer system is configured to initially build a first digital model in memory for identifying a region capturing a leaf, and a second model for identifying a region capturing a leaf infected with a disease. Given a large FoV image, under program control, the system is programmed to then automatically identify candidate regions that might capture single leaves from the large FoV image using the first model. The system is programmed to further determine whether the candidate regions capture symptoms of a crop disease on single leaves using on the second model.

A large FoV image of a crop field can capture tens to hundreds of leaves. As the size of the field of view is unknown, the system is programmed to examine the large FoV image in different scales and apply the first model to each of the scaled images to identify the candidate regions. The first model can include or communicate with a module that computes a histogram of oriented gradients ("HOG") value for a region and further include a support vector machine ("SVM") that determines whether the region captures a leaf based on the HOG value. The SVM can be trained with images having a certain size that mainly capture single leaves. Specifically, the system is programmed to execute the first model on each scaled image to compute the HOG for each sliding window of the scaled image having that certain size and to classify the corresponding region using the HOG value to determine whether the corresponding region is a candidate region likely to capture a leaf.

Aside from the HOG values for recognizing leaves, additional features can be computed for each candidate region for recognizing crop disease symptoms on leaves. The second model can include a convolutional neural network ("CNN") that includes a set of convolutional layer that computes feature maps associated with an infected leaf for an area and a fully-connected layer for determining whether the area or a region within the area captures an infected leaf based on the feature maps. The CNN can also include an additional region-of-interest ("RoI") pooling layer before the fully-connected layer. Training data for the CNN can be seeded with an initial set of images having a certain size that capture infected and healthy leaves at various scales. The training data can then be augmented with variants of the initial set of images through rotation, shearing, and application of an improved Wassersstein generative adversarial network ("WGAN"). Instead of computing the additional features for different candidate regions separately, the system is programmed to process the large FoV image using the second model once to identify the additional features for the entire image and perform classification for each of the candidate region by extracting the additional features for the candidate region from the additional features for the entire image.

Specifically, the system is programmed to execute the set of convolutional layers on the large FoV image to generate a set of feature maps for the FoV image. Next, the system is programmed to map the candidate region back to the large FoV image to obtain a mapped region, extract a corresponding portion of each of the set of feature maps based on the mapping, and execute the RoI pooling layer and the fully connected layer on the set of portions of the features maps to determine whether the mapped region is an intermediate region likely to capture an infected leaf. Finally, as some intermediate regions may overlap, the system is programmed to merge some of the intermediate regions into a final region likely to capture an infected leaf.

The system produces many technical benefits. In an embodiment, the system analyzes a large FoV image in two stages, applying efficient and robust computational algorithms in each stage to achieve intended purposes. This systematic approach allows a fast and accurate focus on candidate regions likely to capture intended targets. For example, instead of directly looking in every window of the large FoV image, the system is programmed to first identify certain regions likely to contain single leaves and only look in those regions for infected leaves, using a relatively basic classifier to identify regions capturing single leaves and an advanced classifier to recognize regions capturing infected leaves. The choice of an SVM classifier of HOG feature vectors appears to outperform many previous methods in efficiently identifying regions capturing single leaves from a large FoV image capturing multiple leaves and crops. In maintaining a layered, incremental framework to achieve an optimal combination of high speed and high quality, however, the systematic approach also offers flexibility within each layer to accommodate a potentially wide range of computational techniques. Furthermore, the system applies a variety of specific techniques to achieve the optimal combination of efficiency and accuracy. For example, the system is programmed to take a large FoV image of any size and resize the image internally to find infected leaves of a variable size. Moreover, all relevant features of the large FoV image can be computed in one pass and the individual processing of focus regions is pushed to the last few stages of the analytical pipeline.

2. Example Agricultural Intelligence Computer System

2.1 Structural Overview

FIG. 1 illustrates an example computer system that is configured to perform the functions described herein, shown in a field environment with other apparatus with which the system may interoperate. In one embodiment, a user 102 owns, operates or possesses a field manager computing device 104 in a field location or associated with a field location such as a field intended for agricultural activities or a management location for one or more agricultural fields. The field manager computer device 104 is programmed or configured to provide field data 106 to an agricultural intelligence computer system 130 via one or more networks 109.

Examples of field data 106 include (a) identification data (for example, acreage, field name, field identifiers, geographic identifiers, boundary identifiers, crop identifiers, and any other suitable data that may be used to identify farm land, such as a common land unit (CLU), lot and block number, a parcel number, geographic coordinates and boundaries, Farm Serial Number (FSN), farm number, tract number, field number, section, township, and/or range), (b) harvest data (for example, crop type, crop variety, crop rotation, whether the crop is grown organically, harvest date, Actual Production History (APH), expected yield, yield, crop price, crop revenue, grain moisture, tillage practice, and previous growing season information), (c) soil data (for example, type, composition, pH, organic matter (OM), cation exchange capacity (CEC)), (d) planting data (for example, planting date, seed(s) type, relative maturity (RM) of planted seed(s), seed population), (e) fertilizer data (for example, nutrient type (Nitrogen, Phosphorous, Potassium), application type, application date, amount, source, method), (f) chemical application data (for example, pesticide, herbicide, fungicide, other substance or mixture of substances intended for use as a plant regulator, defoliant, or desiccant, application date, amount, source, method), (g) irrigation data (for example, application date, amount, source, method), (h) weather data (for example, precipitation, rainfall rate, predicted rainfall, water runoff rate region, temperature, wind, forecast, pressure, visibility, clouds, heat index, dew point, humidity, snow depth, air quality, sunrise, sunset), (i) imagery data (for example, imagery and light spectrum information from an agricultural apparatus sensor, camera, computer, smartphone, tablet, unmanned aerial vehicle, planes or satellite), (j) scouting observations (photos, videos, free form notes, voice recordings, voice transcriptions, weather conditions (temperature, precipitation (current and over time), soil moisture, crop growth stage, wind velocity, relative humidity, dew point, black layer)), and (k) soil, seed, crop phenology, pest and disease reporting, and predictions sources and databases.

A data server computer 108 is communicatively coupled to agricultural intelligence computer system 130 and is programmed or configured to send external data 110 to agricultural intelligence computer system 130 via the network(s) 109. The external data server computer 108 may be owned or operated by the same legal person or entity as the agricultural intelligence computer system 130, or by a different person or entity such as a government agency, non-governmental organization (NGO), and/or a private data service provider. Examples of external data include weather data, imagery data, soil data, or statistical data relating to crop yields, among others. External data 110 may consist of the same type of information as field data 106. In some embodiments, the external data 110 is provided by an external data server 108 owned by the same entity that owns and/or operates the agricultural intelligence computer system 130. For example, the agricultural intelligence computer system 130 may include a data server focused exclusively on a type of data that might otherwise be obtained from third party sources, such as weather data. In some embodiments, an external data server 108 may actually be incorporated within the system 130.

An agricultural apparatus 111 may have one or more remote sensors 112 fixed thereon, which sensors are communicatively coupled either directly or indirectly via agricultural apparatus 111 to the agricultural intelligence computer system 130 and are programmed or configured to send sensor data to agricultural intelligence computer system 130. Examples of agricultural apparatus 111 include tractors, combines, harvesters, planters, trucks, fertilizer equipment, aerial vehicles including unmanned aerial vehicles, and any other item of physical machinery or hardware, typically mobile machinery, and which may be used in tasks associated with agriculture. In some embodiments, a single unit of apparatus 111 may comprise a plurality of sensors 112 that are coupled locally in a network on the apparatus; controller area network (CAN) is example of such a network that can be installed in combines, harvesters, sprayers, and cultivators. Application controller 114 is communicatively coupled to agricultural intelligence computer system 130 via the network(s) 109 and is programmed or configured to receive one or more scripts that are used to control an operating parameter of an agricultural vehicle or implement from the agricultural intelligence computer system 130. For instance, a controller area network (CAN) bus interface may be used to enable communications from the agricultural intelligence computer system 130 to the agricultural apparatus 111, such as how the CLIMATE FIELDVIEW DRIVE, available from The Climate Corporation, San Francisco, Calif., is used. Sensor data may consist of the same type of information as field data 106. In some embodiments, remote sensors 112 may not be fixed to an agricultural apparatus 111 but may be remotely located in the field and may communicate with network 109.

The apparatus 111 may comprise a cab computer 115 that is programmed with a cab application, which may comprise a version or variant of the mobile application for device 104 that is further described in other sections herein. In an embodiment, cab computer 115 comprises a compact computer, often a tablet-sized computer or smartphone, with a graphical screen display, such as a color display, that is mounted within an operator's cab of the apparatus 111. Cab computer 115 may implement some or all of the operations and functions that are described further herein for the mobile computer device 104.

The network(s) 109 broadly represent any combination of one or more data communication networks including local area networks, wide area networks, internetworks or internets, using any of wireline or wireless links, including terrestrial or satellite links. The network(s) may be implemented by any medium or mechanism that provides for the exchange of data between the various elements of FIG. 1. The various elements of FIG. 1 may also have direct (wired or wireless) communications links. The sensors 112, controller 114, external data server computer 108, and other elements of the system each comprise an interface compatible with the network(s) 109 and are programmed or configured to use standardized protocols for communication across the networks such as TCP/IP, Bluetooth, CAN protocol and higher-layer protocols such as HTTP, TLS, and the like.

Agricultural intelligence computer system 130 is programmed or configured to receive field data 106 from field manager computing device 104, external data 110 from external data server computer 108, and sensor data from remote sensor 112. Agricultural intelligence computer system 130 may be further configured to host, use or execute one or more computer programs, other software elements, digitally programmed logic such as FPGAs or ASICs, or any combination thereof to perform translation and storage of data values, construction of digital models of one or more crops on one or more fields, generation of recommendations and notifications, and generation and sending of scripts to application controller 114, in the manner described further in other sections of this disclosure.

In an embodiment, agricultural intelligence computer system 130 is programmed with or comprises a communication layer 132, presentation layer 134, data management layer 140, hardware/virtualization layer 150, and model and field data repository 160. "Layer," in this context, refers to any combination of electronic digital interface circuits, microcontrollers, firmware such as drivers, and/or computer programs or other software elements.

Communication layer 132 may be programmed or configured to perform input/output interfacing functions including sending requests to field manager computing device 104, external data server computer 108, and remote sensor 112 for field data, external data, and sensor data respectively. Communication layer 132 may be programmed or configured to send the received data to model and field data repository 160 to be stored as field data 106.

Presentation layer 134 may be programmed or configured to generate a graphical user interface (GUI) to be displayed on field manager computing device 104, cab computer 115 or other computers that are coupled to the system 130 through the network 109. The GUI may comprise controls for inputting data to be sent to agricultural intelligence computer system 130, generating requests for models and/or recommendations, and/or displaying recommendations, notifications, models, and other field data.

Data management layer 140 may be programmed or configured to manage read operations and write operations involving the repository 160 and other functional elements of the system, including queries and result sets communicated between the functional elements of the system and the repository. Examples of data management layer 140 include JDBC, SQL server interface code, and/or HADOOP interface code, among others. Repository 160 may comprise a database. As used herein, the term "database" may refer to either a body of data, a relational database management system (RDBMS), or to both. As used herein, a database may comprise any collection of data including hierarchical databases, relational databases, flat file databases, object-relational databases, object oriented databases, distributed databases, and any other structured collection of records or data that is stored in a computer system. Examples of RDBMS's include, but are not limited to including, ORACLE®, MYSQL, IBM® DB2, MICROSOFT® SQL SERVER, SYBASE®, and POSTGRESQL databases. However, any database may be used that enables the systems and methods described herein.

When field data 106 is not provided directly to the agricultural intelligence computer system via one or more agricultural machines or agricultural machine devices that interacts with the agricultural intelligence computer system, the user may be prompted via one or more user interfaces on the user device (served by the agricultural intelligence computer system) to input such information. In an example embodiment, the user may specify identification data by accessing a map on the user device (served by the agricultural intelligence computer system) and selecting specific CLUs that have been graphically shown on the map. In an alternative embodiment, the user 102 may specify identification data by accessing a map on the user device (served by the agricultural intelligence computer system 130) and drawing boundaries of the field over the map. Such CLU selection or map drawings represent geographic identifiers. In alternative embodiments, the user may specify identification data by accessing field identification data (provided as shape files or in a similar format) from the U.S. Department of Agriculture Farm Service Agency or other source via the user device and providing such field identification data to the agricultural intelligence computer system.

In an example embodiment, the agricultural intelligence computer system 130 is programmed to generate and cause displaying a graphical user interface comprising a data manager for data input. After one or more fields have been identified using the methods described above, the data manager may provide one or more graphical user interface widgets which when selected can identify changes to the field, soil, crops, tillage, or nutrient practices. The data manager may include a timeline view, a spreadsheet view, and/or one or more editable programs.

Figure 5:
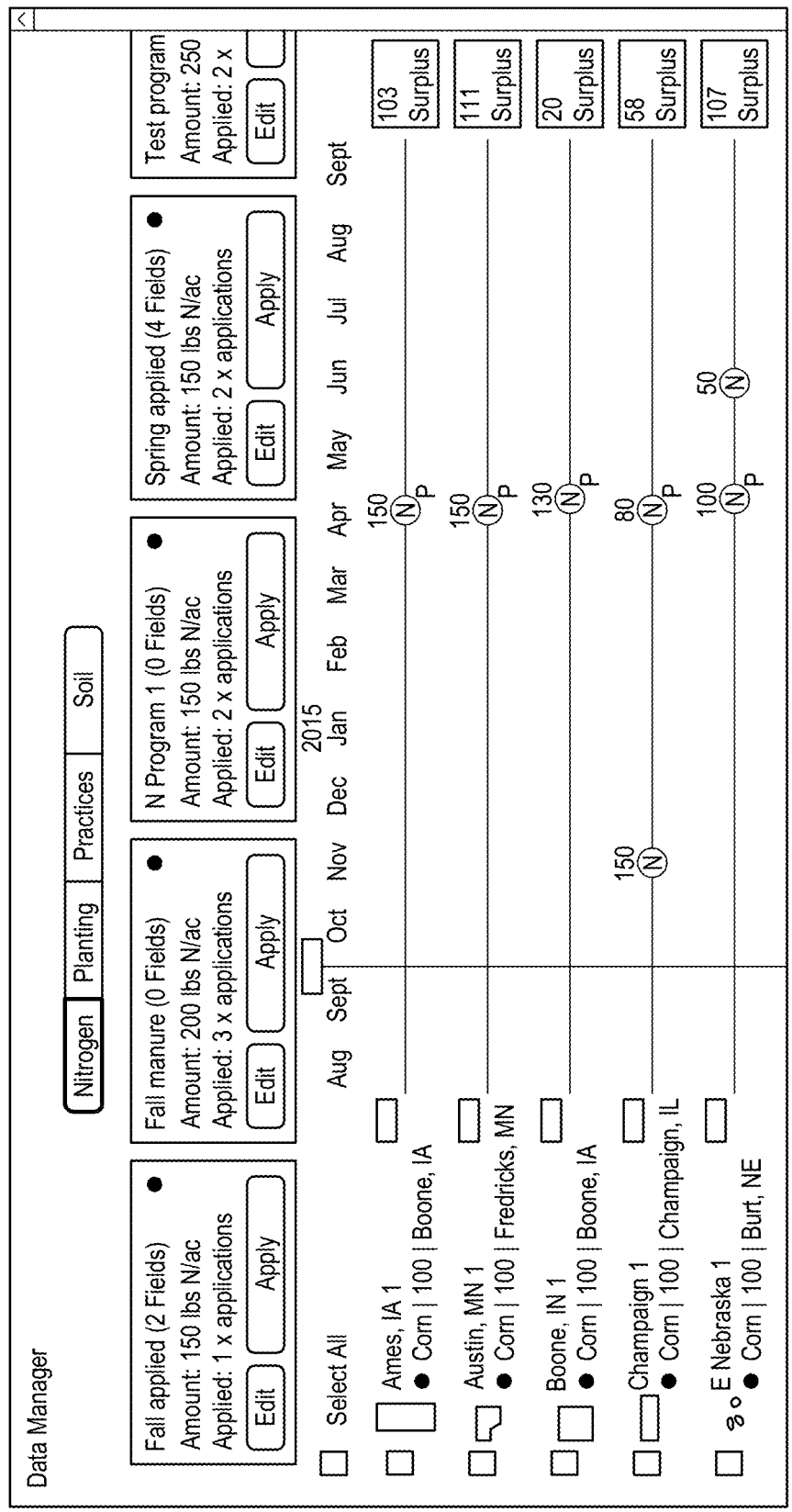
FIG. 5 depicts an example embodiment of a timeline view for data entry.

FIG. 5 depicts an example embodiment of a timeline view for data entry. Using the display depicted in FIG. 5, a user computer can input a selection of a particular field and a particular date for the addition of event. Events depicted at the top of the timeline may include Nitrogen, Planting, Practices, and Soil. To add a nitrogen application event, a user computer may provide input to select the nitrogen tab. The user computer may then select a location on the timeline for a particular field in order to indicate an application of nitrogen on the selected field. In response to receiving a selection of a location on the timeline for a particular field, the data manager may display a data entry overlay, allowing the user computer to input data pertaining to nitrogen applications, planting procedures, soil application, tillage procedures, irrigation practices, or other information relating to the particular field. For example, if a user computer selects a portion of the timeline and indicates an application of nitrogen, then the data entry overlay may include fields for inputting an amount of nitrogen applied, a date of application, a type of fertilizer used, and any other information related to the application of nitrogen.

In an embodiment, the data manager provides an interface for creating one or more programs. "Program," in this context, refers to a set of data pertaining to nitrogen applications, planting procedures, soil application, tillage procedures, irrigation practices, or other information that may be related to one or more fields, and that can be stored in digital data storage for reuse as a set in other operations. After a program has been created, it may be conceptually applied to one or more fields and references to the program may be stored in digital storage in association with data identifying the fields. Thus, instead of manually entering identical data relating to the same nitrogen applications for multiple different fields, a user computer may create a program that indicates a particular application of nitrogen and then apply the program to multiple different fields. For example, in the timeline view of FIG. 5, the top two timelines have the "Spring applied" program selected, which includes an application of 150 lbs N/ac in early April. The data manager may provide an interface for editing a program. In an embodiment, when a particular program is edited, each field that has selected the particular program is edited. For example, in FIG. 5, if the "Spring applied" program is edited to reduce the application of nitrogen to 130 lbs N/ac, the top two fields may be updated with a reduced application of nitrogen based on the edited program.

In an embodiment, in response to receiving edits to a field that has a program selected, the data manager removes the correspondence of the field to the selected program. For example, if a nitrogen application is added to the top field in FIG. 5, the interface may update to indicate that the "Spring applied" program is no longer being applied to the top field. While the nitrogen application in early April may remain, updates to the "Spring applied" program would not alter the April application of nitrogen.

FIG. 6 depicts an example embodiment of a spreadsheet view for data entry. Using the display depicted in FIG. 6, a user can create and edit information for one or more fields. The data manager may include spreadsheets for inputting information with respect to Nitrogen, Planting, Practices, and Soil as depicted in FIG. 6. To edit a particular entry, a user computer may select the particular entry in the spreadsheet and update the values. For example, FIG. 6 depicts an in-progress update to a target yield value for the second field. Additionally, a user computer may select one or more fields in order to apply one or more programs. In response to receiving a selection of a program for a particular field, the data manager may automatically complete the entries for the particular field based on the selected program. As with the timeline view, the data manager may update the entries for each field associated with a particular program in response to receiving an update to the program. Additionally, the data manager may remove the correspondence of the selected program to the field in response to receiving an edit to one of the entries for the field.

In an embodiment, model and field data is stored in model and field data repository 160. Model data comprises data models created for one or more fields. For example, a crop model may include a digitally constructed model of the development of a crop on the one or more fields. "Model," in this context, refers to an electronic digitally stored set of executable instructions and data values, associated with one another, which are capable of receiving and responding to a programmatic or other digital call, invocation, or request for resolution based upon specified input values, to yield one or more stored or calculated output values that can serve as the basis of computer-implemented recommendations, output data displays, or machine control, among other things. Persons of skill in the field find it convenient to express models using mathematical equations, but that form of expression does not confine the models disclosed herein to abstract concepts; instead, each model herein has a practical application in a computer in the form of stored executable instructions and data that implement the model using the computer. The model may include a model of past events on the one or more fields, a model of the current status of the one or more fields, and/or a model of predicted events on the one or more fields. Model and field data may be stored in data structures in memory, rows in a database table, in flat files or spreadsheets, or other forms of stored digital data.

In an embodiment, agricultural intelligence computer system 130 is programmed with or comprises a large FoV disease recognition server computer or instruction set ("server") 170. The server 170 is further configured to comprise a crop identification component 172, a disease recognition component 174, and a client interface 176. The crop identification component 172 is configured to build and execute an object identification model. The object is typically a single leaf of a certain crop but can comprise multiple leaves or other portions of the crop. The object identification model can take a large FoV image and produce information identifying regions of the image likely to capture desired objects. "Large", in this context, means covering more than one object and often at least tens or hundreds of objects. The disease recognition component 174 is configured to build and execute a disease recognition model. As noted above, "model", in this context, refers to an electronic digitally stored set of executable instructions and data values, associated with one another, which are capable of receiving and responding to a programmatic or other digital call, invocation, or request for resolution based upon specified input values, to yield one or more stored or calculated output values that can serve as the basis of computer-implemented recommendations, output data displays, or machine control, among other things. The disease can be any crop disease, such as northern leaf blight ("NLB"), represented by its symptoms on an infected object, such as a corn leaf. The disease recognition model can take a large FoV image and produce information identifying regions of the image likely to capture objects infected with a disease. The client interface 176 is configured to communicate with a client device, such as a field manager computing device 104 or a cab computer 105, over a communication network, through the communication layer 132. The client interface 176 can also be configured to communicate with a display device through the presentation layer 134. The communication can include receiving training data for building the object identification model or the disease recognition model, receiving a large FoV image, or transmitting information identifying regions of a large FoV image likely to capture infected objects.

In an embodiment, each component of the server 170 comprises a set of one or more pages of main memory, such as RAM, in the agricultural intelligence computer system 130 into which executable instructions have been loaded and which when executed cause the agricultural intelligence computing system to perform the functions or operations that are described herein with reference to those modules. For example, the disease recognition component 174 may comprise a set of pages in RAM that contain instructions which when executed cause performing the location selection functions that are described herein. The instructions may be in machine executable code in the instruction set of a CPU and may have been compiled based upon source code written in JAVA, C, C++, OBJECTIVE-C, or any other human-readable programming language or environment, alone or in combination with scripts in JAVASCRIPT, other scripting languages and other programming source text. The term "pages" is intended to refer broadly to any region within main memory and the specific terminology used in a system may vary depending on the memory architecture or processor architecture. In another embodiment, each component of the server 170 also may represent one or more files or projects of source code that are digitally stored in a mass storage device such as non-volatile RAM or disk storage, in the agricultural intelligence computer system 130 or a separate repository system, which when compiled or interpreted cause generating executable instructions which when executed cause the agricultural intelligence computing system to perform the functions or operations that are described herein with reference to those modules. In other words, the drawing figure may represent the manner in which programmers or software developers organize and arrange source code for later compilation into an executable, or interpretation into bytecode or the equivalent, for execution by the agricultural intelligence computer system 130.

Figure 4:
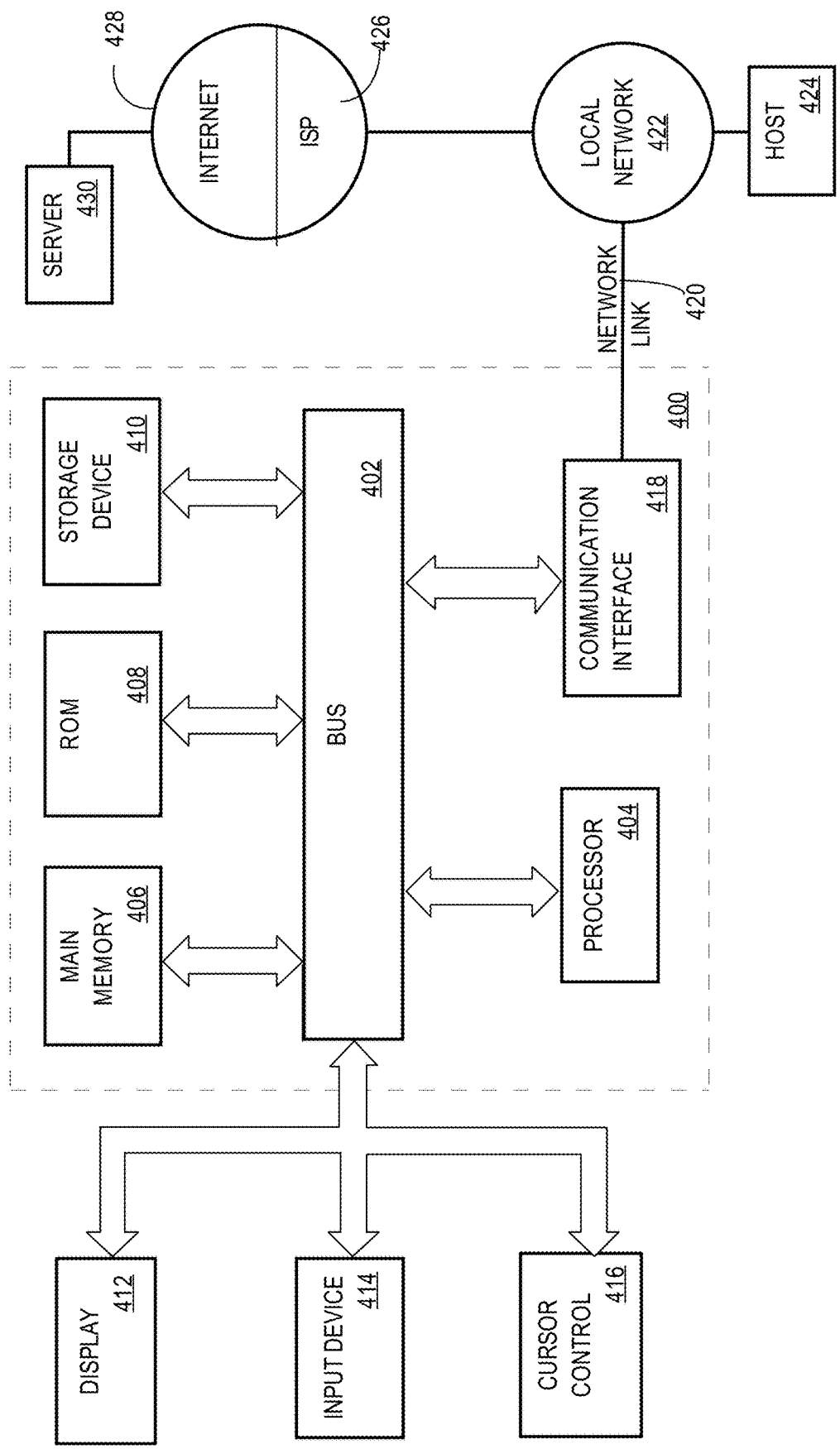
FIG. 4 is a block diagram that illustrates a computer system upon which an embodiment of the invention may be implemented.

Hardware/virtualization layer 150 comprises one or more central processing units (CPUs), memory controllers, and other devices, components, or elements of a computer system such as volatile or non-volatile memory, non-volatile storage such as disk, and I/O devices or interfaces as illustrated and described, for example, in connection with FIG. 4. The layer 150 also may comprise programmed instructions that are configured to support virtualization, containerization, or other technologies.

For purposes of illustrating a clear example, FIG. 1 shows a limited number of instances of certain functional elements. However, in other embodiments, there may be any number of such elements. For example, embodiments may use thousands or millions of different mobile computing devices 104 associated with different users. Further, the system 130 and/or external data server computer 108 may be implemented using two or more processors, cores, clusters, or instances of physical machines or virtual machines, configured in a discrete location or co-located with other elements in a datacenter, shared computing facility or cloud computing facility.

2.2. Application Program Overview

In an embodiment, the implementation of the functions described herein using one or more computer programs or other software elements that are loaded into and executed using one or more general-purpose computers will cause the general-purpose computers to be configured as a particular machine or as a computer that is specially adapted to perform the functions described herein. Further, each of the flow diagrams that are described further herein may serve, alone or in combination with the descriptions of processes and functions in prose herein, as algorithms, plans or directions that may be used to program a computer or logic to implement the functions that are described. In other words, all the prose text herein, and all the drawing figures, together are intended to provide disclosure of algorithms, plans or directions that are sufficient to permit a skilled person to program a computer to perform the functions that are described herein, in combination with the skill and knowledge of such a person given the level of skill that is appropriate for inventions and disclosures of this type.

In an embodiment, user 102 interacts with agricultural intelligence computer system 130 using field manager computing device 104 configured with an operating system and one or more application programs or apps; the field manager computing device 104 also may interoperate with the agricultural intelligence computer system independently and automatically under program control or logical control and direct user interaction is not always required. Field manager computing device 104 broadly represents one or more of a smart phone, PDA, tablet computing device, laptop computer, desktop computer, workstation, or any other computing device capable of transmitting and receiving information and performing the functions described herein. Field manager computing device 104 may communicate via a network using a mobile application stored on field manager computing device 104, and in some embodiments, the device may be coupled using a cable 113 or connector to the sensor 112 and/or controller 114. A particular user 102 may own, operate or possess and use, in connection with system 130, more than one field manager computing device 104 at a time.

The mobile application may provide client-side functionality, via the network to one or more mobile computing devices. In an example embodiment, field manager computing device 104 may access the mobile application via a web browser or a local client application or app. Field manager computing device 104 may transmit data to, and receive data from, one or more front-end servers, using web-based protocols or formats such as HTTP, XML and/or JSON, or app-specific protocols. In an example embodiment, the data may take the form of requests and user information input, such as field data, into the mobile computing device. In some embodiments, the mobile application interacts with location tracking hardware and software on field manager computing device 104 which determines the location of field manager computing device 104 using standard tracking techniques such as multilateration of radio signals, the global positioning system (GPS), WiFi positioning systems, or other methods of mobile positioning. In some cases, location data or other data associated with the device 104, user 102, and/or user account(s) may be obtained by queries to an operating system of the device or by requesting an app on the device to obtain data from the operating system.

In an embodiment, field manager computing device 104 sends field data 106 to agricultural intelligence computer system 130 comprising or including, but not limited to, data values representing one or more of: a geographical location of the one or more fields, tillage information for the one or more fields, crops planted in the one or more fields, and soil data extracted from the one or more fields. Field manager computing device 104 may send field data 106 in response to user input from user 102 specifying the data values for the one or more fields. Additionally, field manager computing device 104 may automatically send field data 106 when one or more of the data values becomes available to field manager computing device 104. For example, field manager computing device 104 may be communicatively coupled to remote sensor 112 and/or application controller 114 which include an irrigation sensor and/or irrigation controller. In response to receiving data indicating that application controller 114 released water onto the one or more fields, field manager computing device 104 may send field data 106 to agricultural intelligence computer system 130 indicating that water was released on the one or more fields. Field data 106 identified in this disclosure may be input and communicated using electronic digital data that is communicated between computing devices using parameterized URLs over HTTP, or another suitable communication or messaging protocol.

A commercial example of the mobile application is CLIMATE FIELDVIEW, commercially available from The Climate Corporation, San Francisco, Calif. The CLIMATE FIELDVIEW application, or other applications, may be modified, extended, or adapted to include features, functions, and programming that have not been disclosed earlier than the filing date of this disclosure. In one embodiment, the mobile application comprises an integrated software platform that allows a grower to make fact-based decisions for their operation because it combines historical data about the grower's fields with any other data that the grower wishes to compare. The combinations and comparisons may be performed in real time and are based upon scientific models that provide potential scenarios to permit the grower to make better, more informed decisions.

FIG. 2 illustrates two views of an example logical organization of sets of instructions in main memory when an example mobile application is loaded for execution. In FIG. 2, each named element represents a region of one or more pages of RAM or other main memory, or one or more blocks of disk storage or other non-volatile storage, and the programmed instructions within those regions. In one embodiment, in view (a), a mobile computer application 200 comprises account-fields-data ingestion-sharing instructions 202, overview and alert instructions 204, digital map book instructions 206, seeds and planting instructions 208, nitrogen instructions 210, weather instructions 212, field health instructions 214, and performance instructions 216.

In one embodiment, a mobile computer application 200 comprises account, fields, data ingestion, sharing instructions 202 which are programmed to receive, translate, and ingest field data from third party systems via manual upload or APIs. Data types may include field boundaries, yield maps, as-planted maps, soil test results, as-applied maps, and/or management zones, among others. Data formats may include shape files, native data formats of third parties, and/or farm management information system (FMIS) exports, among others. Receiving data may occur via manual upload, e-mail with attachment, external APIs that push data to the mobile application, or instructions that call APIs of external systems to pull data into the mobile application. In one embodiment, mobile computer application 200 comprises a data inbox. In response to receiving a selection of the data inbox, the mobile computer application 200 may display a graphical user interface for manually uploading data files and importing uploaded files to a data manager.

In one embodiment, digital map book instructions 206 comprise field map data layers stored in device memory and are programmed with data visualization tools and geospatial field notes. This provides growers with convenient information close at hand for reference, logging and visual insights into field performance. In one embodiment, overview and alert instructions 204 are programmed to provide an operation-wide view of what is important to the grower, and timely recommendations to take action or focus on particular issues. This permits the grower to focus time on what needs attention, to save time and preserve yield throughout the season. In one embodiment, seeds and planting instructions 208 are programmed to provide tools for seed selection, hybrid placement, and script creation, including variable rate (VR) script creation, based upon scientific models and empirical data. This enables growers to maximize yield or return on investment through optimized seed purchase, placement and population.

In one embodiment, script generation instructions 205 are programmed to provide an interface for generating scripts, including variable rate (VR) fertility scripts. The interface enables growers to create scripts for field implements, such as nutrient applications, planting, and irrigation. For example, a planting script interface may comprise tools for identifying a type of seed for planting. Upon receiving a selection of the seed type, mobile computer application 200 may display one or more fields broken into management zones, such as the field map data layers created as part of digital map book instructions 206. In one embodiment, the management zones comprise soil zones along with a panel identifying each soil zone and a soil name, texture, drainage for each zone, or other field data. Mobile computer application 200 may also display tools for editing or creating such, such as graphical tools for drawing management zones, such as soil zones, over a map of one or more fields. Planting procedures may be applied to all management zones or different planting procedures may be applied to different subsets of management zones. When a script is created, mobile computer application 200 may make the script available for download in a format readable by an application controller, such as an archived or compressed format. Additionally, and/or alternatively, a script may be sent directly to cab computer 115 from mobile computer application 200 and/or uploaded to one or more data servers and stored for further use.

In one embodiment, nitrogen instructions 210 are programmed to provide tools to inform nitrogen decisions by visualizing the availability of nitrogen to crops. This enables growers to maximize yield or return on investment through optimized nitrogen application during the season. Example programmed functions include displaying images such as SSURGO images to enable drawing of fertilizer application zones and/or images generated from subfield soil data, such as data obtained from sensors, at a high spatial resolution (as fine as millimeters or smaller depending on sensor proximity and resolution); upload of existing grower-defined zones; providing a graph of plant nutrient availability and/or a map to enable tuning application(s) of nitrogen across multiple zones; output of scripts to drive machinery; tools for mass data entry and adjustment; and/or maps for data visualization, among others. "Mass data entry," in this context, may mean entering data once and then applying the same data to multiple fields and/or zones that have been defined in the system; example data may include nitrogen application data that is the same for many fields and/or zones of the same grower, but such mass data entry applies to the entry of any type of field data into the mobile computer application 200. For example, nitrogen instructions 210 may be programmed to accept definitions of nitrogen application and practices programs and to accept user input specifying to apply those programs across multiple fields. "Nitrogen application programs," in this context, refers to stored, named sets of data that associates: a name, color code or other identifier, one or more dates of application, types of material or product for each of the dates and amounts, method of application or incorporation such as injected or broadcast, and/or amounts or rates of application for each of the dates, crop or hybrid that is the subject of the application, among others. "Nitrogen practices programs," in this context, refer to stored, named sets of data that associates: a practices name; a previous crop; a tillage system; a date of primarily tillage; one or more previous tillage systems that were used; one or more indicators of application type, such as manure, that were used. Nitrogen instructions 210 also may be programmed to generate and cause displaying a nitrogen graph, which indicates projections of plant use of the specified nitrogen and whether a surplus or shortfall is predicted; in some embodiments, different color indicators may signal a magnitude of surplus or magnitude of shortfall. In one embodiment, a nitrogen graph comprises a graphical display in a computer display device comprising a plurality of rows, each row associated with and identifying a field; data specifying what crop is planted in the field, the field size, the field location, and a graphic representation of the field perimeter; in each row, a timeline by month with graphic indicators specifying each nitrogen application and amount at points correlated to month names; and numeric and/or colored indicators of surplus or shortfall, in which color indicates magnitude.

In one embodiment, the nitrogen graph may include one or more user input features, such as dials or slider bars, to dynamically change the nitrogen planting and practices programs so that a user may optimize his nitrogen graph. The user may then use his optimized nitrogen graph and the related nitrogen planting and practices programs to implement one or more scripts, including variable rate (VR) fertility scripts. Nitrogen instructions 210 also may be programmed to generate and cause displaying a nitrogen map, which indicates projections of plant use of the specified nitrogen and whether a surplus or shortfall is predicted; in some embodiments, different color indicators may signal a magnitude of surplus or magnitude of shortfall. The nitrogen map may display projections of plant use of the specified nitrogen and whether a surplus or shortfall is predicted for different times in the past and the future (such as daily, weekly, monthly or yearly) using numeric and/or colored indicators of surplus or shortfall, in which color indicates magnitude. In one embodiment, the nitrogen map may include one or more user input features, such as dials or slider bars, to dynamically change the nitrogen planting and practices programs so that a user may optimize his nitrogen map, such as to obtain a preferred amount of surplus to shortfall. The user may then use his optimized nitrogen map and the related nitrogen planting and practices programs to implement one or more scripts, including variable rate (VR) fertility scripts. In other embodiments, similar instructions to the nitrogen instructions 210 could be used for application of other nutrients (such as phosphorus and potassium), application of pesticide, and irrigation programs.

In one embodiment, weather instructions 212 are programmed to provide field-specific recent weather data and forecasted weather information. This enables growers to save time and have an efficient integrated display with respect to daily operational decisions.

In one embodiment, field health instructions 214 are programmed to provide timely remote sensing images highlighting in-season crop variation and potential concerns. Example programmed functions include cloud checking, to identify possible clouds or cloud shadows; determining nitrogen indices based on field images; graphical visualization of scouting layers, including, for example, those related to field health, and viewing and/or sharing of scouting notes; and/or downloading satellite images from multiple sources and prioritizing the images for the grower, among others.

In one embodiment, performance instructions 216 are programmed to provide reports, analysis, and insight tools using on-farm data for evaluation, insights and decisions. This enables the grower to seek improved outcomes for the next year through fact-based conclusions about why return on investment was at prior levels, and insight into yield-limiting factors. The performance instructions 216 may be programmed to communicate via the network(s) 109 to back-end analytics programs executed at agricultural intelligence computer system 130 and/or external data server computer 108 and configured to analyze metrics such as yield, yield differential, hybrid, population, SSURGO zone, soil test properties, or elevation, among others. Programmed reports and analysis may include yield variability analysis, treatment effect estimation, benchmarking of yield and other metrics against other growers based on anonymized data collected from many growers, or data for seeds and planting, among others.

Applications having instructions configured in this way may be implemented for different computing device platforms while retaining the same general user interface appearance. For example, the mobile application may be programmed for execution on tablets, smartphones, or server computers that are accessed using browsers at client computers. Further, the mobile application as configured for tablet computers or smartphones may provide a full app experience or a cab app experience that is suitable for the display and processing capabilities of cab computer 115. For example, referring now to view (b) of FIG. 2, in one embodiment a cab computer application 220 may comprise maps-cab instructions 222, remote view instructions 224, data collect and transfer instructions 226, machine alerts instructions 228, script transfer instructions 230, and scouting-cab instructions 232. The code base for the instructions of view (b) may be the same as for view (a) and executables implementing the code may be programmed to detect the type of platform on which they are executing and to expose, through a graphical user interface, only those functions that are appropriate to a cab platform or full platform. This approach enables the system to recognize the distinctly different user experience that is appropriate for an in-cab environment and the different technology environment of the cab. The maps-cab instructions 222 may be programmed to provide map views of fields, farms or regions that are useful in directing machine operation. The remote view instructions 224 may be programmed to turn on, manage, and provide views of machine activity in real-time or near real-time to other computing devices connected to the system 130 via wireless networks, wired connectors or adapters, and the like. The data collect and transfer instructions 226 may be programmed to turn on, manage, and provide transfer of data collected at sensors and controllers to the system 130 via wireless networks, wired connectors or adapters, and the like. The machine alerts instructions 228 may be programmed to detect issues with operations of the machine or tools that are associated with the cab and generate operator alerts. The script transfer instructions 230 may be configured to transfer in scripts of instructions that are configured to direct machine operations or the collection of data. The scouting-cab instructions 232 may be programmed to display location-based alerts and information received from the system 130 based on the location of the field manager computing device 104, agricultural apparatus 111, or sensors 112 in the field and ingest, manage, and provide transfer of location-based scouting observations to the system 130 based on the location of the agricultural apparatus 111 or sensors 112 in the field.

2.3. Data Ingest to the Computer System

In an embodiment, external data server computer 108 stores external data 110, including soil data representing soil composition for the one or more fields and weather data representing temperature and precipitation on the one or more fields. The weather data may include past and present weather data as well as forecasts for future weather data. In an embodiment, external data server computer 108 comprises a plurality of servers hosted by different entities. For example, a first server may contain soil composition data while a second server may include weather data. Additionally, soil composition data may be stored in multiple servers. For example, one server may store data representing percentage of sand, silt, and clay in the soil while a second server may store data representing percentage of organic matter (OM) in the soil.

In an embodiment, remote sensor 112 comprises one or more sensors that are programmed or configured to produce one or more observations. Remote sensor 112 may be aerial sensors, such as satellites, vehicle sensors, planting equipment sensors, tillage sensors, fertilizer or insecticide application sensors, harvester sensors, and any other implement capable of receiving data from the one or more fields. In an embodiment, application controller 114 is programmed or configured to receive instructions from agricultural intelligence computer system 130. Application controller 114 may also be programmed or configured to control an operating parameter of an agricultural vehicle or implement. For example, an application controller may be programmed or configured to control an operating parameter of a vehicle, such as a tractor, planting equipment, tillage equipment, fertilizer or insecticide equipment, harvester equipment, or other farm implements such as a water valve. Other embodiments may use any combination of sensors and controllers, of which the following are merely selected examples.

The system 130 may obtain or ingest data under user 102 control, on a mass basis from a large number of growers who have contributed data to a shared database system. This form of obtaining data may be termed "manual data ingest" as one or more user-controlled computer operations are requested or triggered to obtain data for use by the system 130. As an example, the CLIMATE FIELDVIEW application, commercially available from The Climate Corporation, San Francisco, Calif., may be operated to export data to system 130 for storing in the repository 160.

For example, seed monitor systems can both control planter apparatus components and obtain planting data, including signals from seed sensors via a signal harness that comprises a CAN backbone and point-to-point connections for registration and/or diagnostics. Seed monitor systems can be programmed or configured to display seed spacing, population and other information to the user via the cab computer 115 or other devices within the system 130. Examples are disclosed in U.S. Pat. No. 8,738,243 and US Pat. Pub. 20150094916, and the present disclosure assumes knowledge of those other patent disclosures.

Likewise, yield monitor systems may contain yield sensors for harvester apparatus that send yield measurement data to the cab computer 115 or other devices within the system 130. Yield monitor systems may utilize one or more remote sensors 112 to obtain grain moisture measurements in a combine or other harvester and transmit these measurements to the user via the cab computer 115 or other devices within the system 130.

In an embodiment, examples of sensors 112 that may be used with any moving vehicle or apparatus of the type described elsewhere herein include kinematic sensors and position sensors. Kinematic sensors may comprise any of speed sensors such as radar or wheel speed sensors, accelerometers, or gyros. Position sensors may comprise GPS receivers or transceivers, or WiFi-based position or mapping apps that are programmed to determine location based upon nearby WiFi hotspots, among others.

In an embodiment, examples of sensors 112 that may be used with tractors or other moving vehicles include engine speed sensors, fuel consumption sensors, area counters or distance counters that interact with GPS or radar signals, PTO (power take-off) speed sensors, tractor hydraulics sensors configured to detect hydraulics parameters such as pressure or flow, and/or and hydraulic pump speed, wheel speed sensors or wheel slippage sensors. In an embodiment, examples of controllers 114 that may be used with tractors include hydraulic directional controllers, pressure controllers, and/or flow controllers; hydraulic pump speed controllers; speed controllers or governors; hitch position controllers; or wheel position controllers provide automatic steering.

In an embodiment, examples of sensors 112 that may be used with seed planting equipment such as planters, drills, or air seeders include seed sensors, which may be optical, electromagnetic, or impact sensors; downforce sensors such as load pins, load cells, pressure sensors; soil property sensors such as reflectivity sensors, moisture sensors, electrical conductivity sensors, optical residue sensors, or temperature sensors; component operating criteria sensors such as planting depth sensors, downforce cylinder pressure sensors, seed disc speed sensors, seed drive motor encoders, seed conveyor system speed sensors, or vacuum level sensors; or pesticide application sensors such as optical or other electromagnetic sensors, or impact sensors. In an embodiment, examples of controllers 114 that may be used with such seed planting equipment include: toolbar fold controllers, such as controllers for valves associated with hydraulic cylinders; downforce controllers, such as controllers for valves associated with pneumatic cylinders, airbags, or hydraulic cylinders, and programmed for applying downforce to individual row units or an entire planter frame; planting depth controllers, such as linear actuators; metering controllers, such as electric seed meter drive motors, hydraulic seed meter drive motors, or swath control clutches; hybrid selection controllers, such as seed meter drive motors, or other actuators programmed for selectively allowing or preventing seed or an air-seed mixture from delivering seed to or from seed meters or central bulk hoppers; metering controllers, such as electric seed meter drive motors, or hydraulic seed meter drive motors; seed conveyor system controllers, such as controllers for a belt seed delivery conveyor motor; marker controllers, such as a controller for a pneumatic or hydraulic actuator; or pesticide application rate controllers, such as metering drive controllers, orifice size or position controllers.

In an embodiment, examples of sensors 112 that may be used with tillage equipment include position sensors for tools such as shanks or discs; tool position sensors for such tools that are configured to detect depth, gang angle, or lateral spacing; downforce sensors; or draft force sensors. In an embodiment, examples of controllers 114 that may be used with tillage equipment include downforce controllers or tool position controllers, such as controllers configured to control tool depth, gang angle, or lateral spacing.

In an embodiment, examples of sensors 112 that may be used in relation to apparatus for applying fertilizer, insecticide, fungicide and the like, such as on-planter starter fertilizer systems, subsoil fertilizer applicators, or fertilizer sprayers, include: fluid system criteria sensors, such as flow sensors or pressure sensors; sensors indicating which spray head valves or fluid line valves are open; sensors associated with tanks, such as fill level sensors; sectional or system-wide supply line sensors, or row-specific supply line sensors; or kinematic sensors such as accelerometers disposed on sprayer booms. In an embodiment, examples of controllers 114 that may be used with such apparatus include pump speed controllers; valve controllers that are programmed to control pressure, flow, direction, PWM and the like; or position actuators, such as for boom height, subsoiler depth, or boom position.

In an embodiment, examples of sensors 112 that may be used with harvesters include yield monitors, such as impact plate strain gauges or position sensors, capacitive flow sensors, load sensors, weight sensors, or torque sensors associated with elevators or augers, or optical or other electromagnetic grain height sensors; grain moisture sensors, such as capacitive sensors; grain loss sensors, including impact, optical, or capacitive sensors; header operating criteria sensors such as header height, header type, deck plate gap, feeder speed, and reel speed sensors; separator operating criteria sensors, such as concave clearance, rotor speed, shoe clearance, or chaffer clearance sensors; auger sensors for position, operation, or speed; or engine speed sensors. In an embodiment, examples of controllers 114 that may be used with harvesters include header operating criteria controllers for elements such as header height, header type, deck plate gap, feeder speed, or reel speed; separator operating criteria controllers for features such as concave clearance, rotor speed, shoe clearance, or chaffer clearance; or controllers for auger position, operation, or speed.

In an embodiment, examples of sensors 112 that may be used with grain carts include weight sensors, or sensors for auger position, operation, or speed. In an embodiment, examples of controllers 114 that may be used with grain carts include controllers for auger position, operation, or speed.

In an embodiment, examples of sensors 112 and controllers 114 may be installed in unmanned aerial vehicle (UAV) apparatus or "drones." Such sensors may include cameras with detectors effective for any range of the electromagnetic spectrum including visible light, infrared, ultraviolet, near-infrared (NIR), and the like; accelerometers; altimeters; temperature sensors; humidity sensors; pitot tube sensors or other airspeed or wind velocity sensors; battery life sensors; or radar emitters and reflected radar energy detection apparatus; other electromagnetic radiation emitters and reflected electromagnetic radiation detection apparatus. Such controllers may include guidance or motor control apparatus, control surface controllers, camera controllers, or controllers programmed to turn on, operate, obtain data from, manage and configure any of the foregoing sensors. Examples are disclosed in U.S. patent application Ser. No. 14/831,165 and the present disclosure assumes knowledge of that other patent disclosure.

In an embodiment, sensors 112 and controllers 114 may be affixed to soil sampling and measurement apparatus that is configured or programmed to sample soil and perform soil chemistry tests, soil moisture tests, and other tests pertaining to soil. For example, the apparatus disclosed in U.S. Pat. Nos. 8,767,194 and 8,712,148 may be used, and the present disclosure assumes knowledge of those patent disclosures.

In an embodiment, sensors 112 and controllers 114 may comprise weather devices for monitoring weather conditions of fields. For example, the apparatus disclosed in U.S. Provisional Application No. 62/154,207, filed on Apr. 29, 2015, U.S. Provisional Application No. 62/175,160, filed on Jun. 12, 2015, U.S. Provisional Application No. 62/198,060, filed on Jul. 28, 2015, and U.S. Provisional Application No. 62/220,852, filed on Sep. 18, 2015, may be used, and the present disclosure assumes knowledge of those patent disclosures.

2.4. Process Overview—Agronomic Model Training

In an embodiment, the agricultural intelligence computer system 130 is programmed or configured to create an agronomic model. In this context, an agronomic model is a data structure in memory of the agricultural intelligence computer system 130 that comprises field data 106, such as identification data and harvest data for one or more fields. The agronomic model may also comprise calculated agronomic properties which describe either conditions which may affect the growth of one or more crops on a field, or properties of the one or more crops, or both. Additionally, an agronomic model may comprise recommendations based on agronomic factors such as crop recommendations, irrigation recommendations, planting recommendations, fertilizer recommendations, fungicide recommendations, pesticide recommendations, harvesting recommendations and other crop management recommendations. The agronomic factors may also be used to estimate one or more crop related results, such as agronomic yield. The agronomic yield of a crop is an estimate of quantity of the crop that is produced, or in some examples the revenue or profit obtained from the produced crop.

In an embodiment, the agricultural intelligence computer system 130 may use a preconfigured agronomic model to calculate agronomic properties related to currently received location and crop information for one or more fields. The preconfigured agronomic model is based upon previously processed field data, including but not limited to, identification data, harvest data, fertilizer data, and weather data. The preconfigured agronomic model may have been cross validated to ensure accuracy of the model. Cross validation may include comparison to ground truthing that compares predicted results with actual results on a field, such as a comparison of precipitation estimate with a rain gauge or sensor providing weather data at the same or nearby location or an estimate of nitrogen content with a soil sample measurement.

Figure 3:
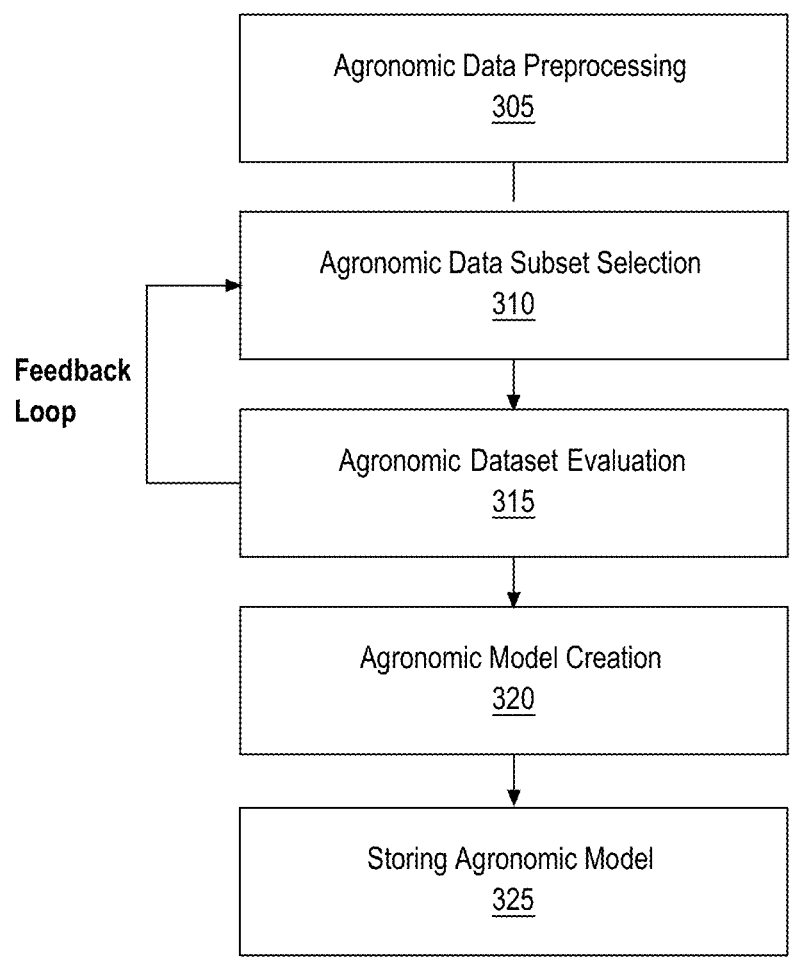
FIG. 3 illustrates a programmed process by which the agricultural intelligence computer system generates one or more preconfigured agronomic models using agronomic data provided by one or more data sources.

FIG. 3 illustrates a programmed process by which the agricultural intelligence computer system generates one or more preconfigured agronomic models using field data provided by one or more data sources. FIG. 3 may serve as an algorithm or instructions for programming the functional elements of the agricultural intelligence computer system 130 to perform the operations that are now described.

At block 305, the agricultural intelligence computer system 130 is configured or programmed to implement agronomic data preprocessing of field data received from one or more data sources. The field data received from one or more data sources may be preprocessed for the purpose of removing noise, distorting effects, and confounding factors within the agronomic data including measured outliers that could adversely affect received field data values. Embodiments of agronomic data preprocessing may include, but are not limited to, removing data values commonly associated with outlier data values, specific measured data points that are known to unnecessarily skew other data values, data smoothing, aggregation, or sampling techniques used to remove or reduce additive or multiplicative effects from noise, and other filtering or data derivation techniques used to provide clear distinctions between positive and negative data inputs.

At block 310, the agricultural intelligence computer system 130 is configured or programmed to perform data subset selection using the preprocessed field data in order to identify datasets useful for initial agronomic model generation. The agricultural intelligence computer system 130 may implement data subset selection techniques including, but not limited to, a genetic algorithm method, an all subset models method, a sequential search method, a stepwise regression method, a particle swarm optimization method, and an ant colony optimization method. For example, a genetic algorithm selection technique uses an adaptive heuristic search algorithm, based on evolutionary principles of natural selection and genetics, to determine and evaluate datasets within the preprocessed agronomic data.

At block 315, the agricultural intelligence computer system 130 is configured or programmed to implement field dataset evaluation. In an embodiment, a specific field dataset is evaluated by creating an agronomic model and using specific quality thresholds for the created agronomic model. Agronomic models may be compared and/or validated using one or more comparison techniques, such as, but not limited to, root mean square error with leave-one-out cross validation (RMSECV), mean absolute error, and mean percentage error. For example, RMSECV can cross validate agronomic models by comparing predicted agronomic property values created by the agronomic model against historical agronomic property values collected and analyzed. In an embodiment, the agronomic dataset evaluation logic is used as a feedback loop where agronomic datasets that do not meet configured quality thresholds are used during future data subset selection steps (block 310).

At block 320, the agricultural intelligence computer system 130 is configured or programmed to implement agronomic model creation based upon the cross validated agronomic datasets. In an embodiment, agronomic model creation may implement multivariate regression techniques to create preconfigured agronomic data models.

At block 325, the agricultural intelligence computer system 130 is configured or programmed to store the preconfigured agronomic data models for future field data evaluation.

2.5. Implementation Example—Hardware Overview

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

For example, FIG. 4 is a block diagram that illustrates a computer system 400 upon which an embodiment of the invention may be implemented. Computer system 400 includes a bus 402 or other communication mechanism for communicating information, and a hardware processor 404 coupled with bus 402 for processing information. Hardware processor 404 may be, for example, a general purpose microprocessor.

Computer system 400 also includes a main memory 406, such as a random access memory (RAM) or other dynamic storage device, coupled to bus 402 for storing information and instructions to be executed by processor 404. Main memory 406 also may be used for storing temporary variables or other intermediate information during execution of instructions to be executed by processor 404. Such instructions, when stored in non-transitory storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or solid-state drive is provided and coupled to bus 402 for storing information and instructions.

Computer system 400 may be coupled via bus 402 to a display 412, such as a cathode ray tube (CRT), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane.

Computer system 400 may implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor 404 executing one or more sequences of one or more instructions contained in main memory 406. Such instructions may be read into main memory 406 from another storage medium, such as storage device 410. Execution of the sequences of instructions contained in main memory 406 causes processor 404 to perform the process steps described herein. In alternative embodiments, hard-wired circuitry may be used in place of or in combination with software instructions.

The term "storage media" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage device 410. Volatile media includes dynamic memory, such as main memory 406. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 402. Transmission media can also take the form of acoustic or light waves, such as those generated during radio-wave and infrared data communications.

Various forms of media may be involved in carrying one or more sequences of one or more instructions to processor 404 for execution. For example, the instructions may initially be carried on a magnetic disk or solid-state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infrared signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN. Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

3. Functional Description

3.1 Model Development

In some embodiments, the large FoV disease recognition server 170 is programmed or configured with data structures and/or database records that are arranged to build a first model for identifying a candidate region likely to capture an intended target from a large FoV image. The intended target can be a single leaf, a set of multiple leaves, or a set of multiple crops regardless of the number of leaves. The server 170 is programmed to receive a first set of training images, such as approximately 2,000 images cropped from aerial scouting images of a field. The training images can each have a consistent size, such as 224 pixels by 224 pixels. When the intended target is a single leaf, the training images that serve as positive samples, which can be approximately half of all the training images, are typically bright enough that a computer can detect a single healthy or infected leaf in the center of the image occupying more than 50% of the total area. The remaining images, which might be too dark, capturing multiple leaves, or capturing only the soil ground, would serve as negative samples.

In some embodiments, the server 170 is programmed to next build a first model based on the first set of training images. The first model can be an SVM that accepts an HOG feature vector for a training image and produces an indication of whether the training image captures an intended target. Specifically, training data for the SVM can be the set of HOG features for the training images that serve as positive examples and the set of HOG features for the training images that serve as negative examples.

FIG. 7 illustrates an example computation of HOG feature vectors for regions of a large FoV image. A region 704 can be extracted from a large FoV image 702. Gradient values shown as the black arrows on the region 704 can be computed for the region 704, as further discussed below. These gradient values generally trace the outline of foreground objects in an image, as illustrated by the white arrows on the large FoV image 702. The HOG feature vector for a region, such as the histogram 706 over different gradient values, can thus capture specific shapes of foreground objects in the region.

In some embodiments, the first model can be built using any SVM module or library known to someone skilled in the art. For example, the SVC function in the scikit-learn library can be executed with default parameter values. Alternatively, the first model can include one or more other classification methods, such as the k-nearest neighbor algorithm or a decision tree. Furthermore, the first model does not need to work with HOG feature vectors or otherwise rely on edge detection. For example, the first model can be based on pattern matching that looks for shapes characteristic of a leaf.

In some embodiments, the server 170 is programmed to also build a second model for identifying intermediate regions likely to capture an infected target from a large FoV image. The server 170 is programmed to receive a second set of training images, such as approximately 1,000 images generated by mobile phones of infected leaves for each disease to be recognized, 1,000 healthy leaf images, and 1,000 background images generated from random cropping of aerial scouting images, with each image at or larger than 224 pixels by 224 pixels. As with the first set of training images, when the intended target is a single leaf, the training images that are to serve as positive examples can each contain a single leaf in the center of the image occupying more than 50% of the total area and be sufficiently bright to indicate any disease symptoms. The server 170 can also be programmed to include images of varying sizes and scales in the second set of training images.

In some embodiments, the server 170 can be programmed to refine the second set of training images as required by the second model. The second set of training images can each be trimmed to a fixed size, such as 224 pixels by 224 pixels. The second set of training images can also be augmented by subjecting the existing training images to various image operations. For example, the short edge of each training image can be resized to be between 256 pixels and 384 pixels for scale augmentation, as further discussed below, and the resized image can be randomly chopped down to 224 pixels by 224 pixels. For further example, the training images can be randomly rotated in the (−90 degrees, 90 degrees) range and randomly sheared with a shear factor of 0.2. For multi-size training, also to be further discussed below, the training images can be resized at successively smaller scales and used directly.

In some embodiments, the server 170 is programmed to further augment the second set of training images. The data augmentation can be performed using a generative adversarial network ("GAN"), which can be used to generate photographs that look authentic to human observers and thus is useful for boosting the performance of a machine-learning model by expanding the training dataset. Specifically, a GAN involves a system of two neural networks, namely a generative network and a discriminative network, contesting with each other in a zero-sum game framework. The set of authentic images is used as the training set to the discriminative network, while the generative network produces a set of artificial images that look authentic to human observers. An example GAN is an improved Wassersstein GAN ("WGAN") as described in the article by Gulrajani et al., arXiv:1704.0028v2 [cs.CV] (2015). The current second set of training images can be used as the training set to the discriminative network in a semi-supervised learning fashion.

In some embodiments, the data augmentation can be implemented using any WGAN module or library known to someone skilled in the art. For example, the improved_wgan_training package under the GitHub library can be adapted by replacing the discriminator with a ResNet50 network (to accept training data of certain sizes), which can be implemented using the ResNet50 model of the Keras library compatible with Python 2.7-3.5.

In some embodiments, the server 170 is programmed to next build a second model based on the second set of training images. The second model can be a CNN that accepts a large FoV image and produces a classification for each candidate regions, which can be identified by the first model, indicating whether the region captures symptoms of one of the predetermined crop diseases.

Figure 8:
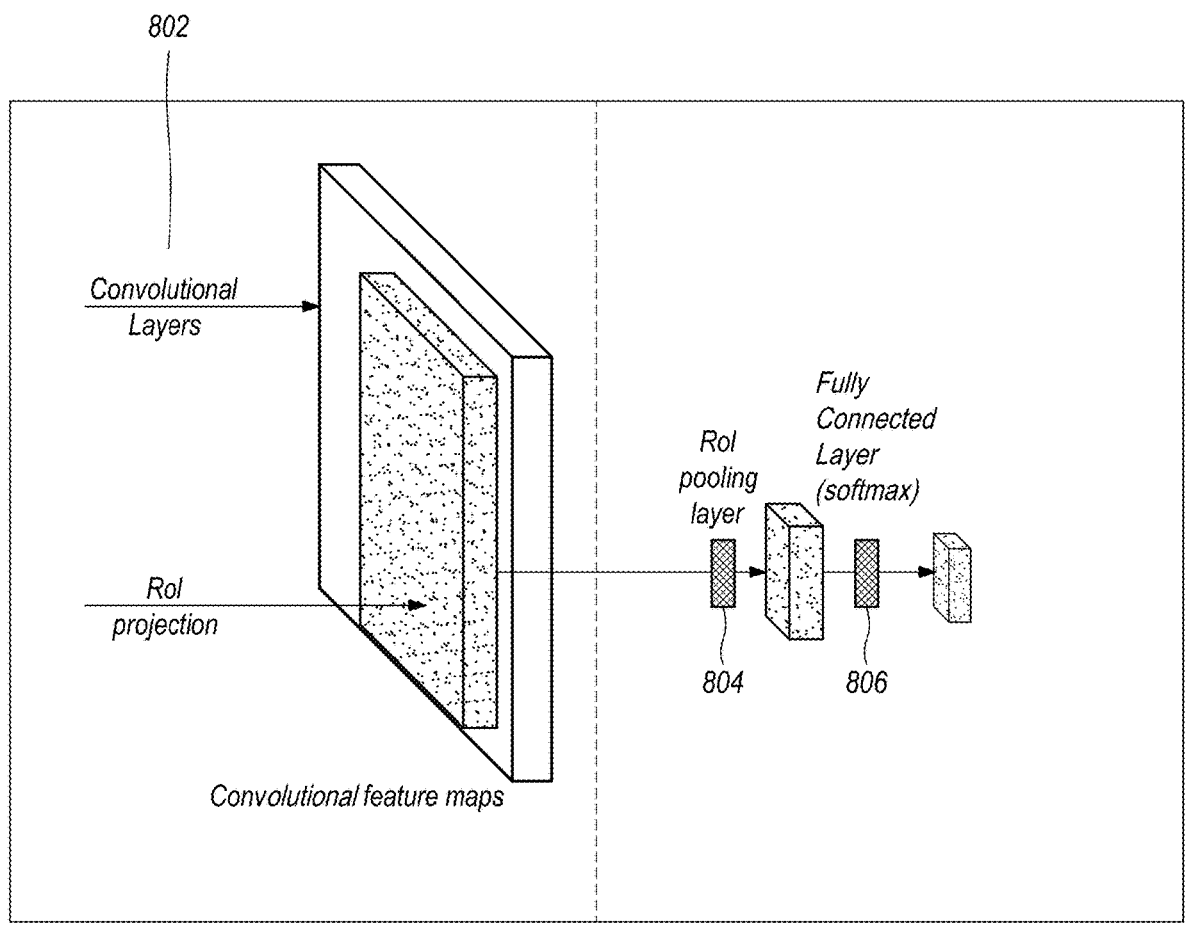
FIG. 8 illustrates an example convolutional neural network architecture.

FIG. 8 illustrates an example CNN architecture according to an embodiment. The CNN can comprise a set of convolutional layers 802 configured to generate feature maps for the given large FoV image. The output of executing the set of convolutional layers is a set of feature maps corresponding to different features of infected targets, which may be at different scales.

The CNN can further comprise an RoI pooling layer 804 to generate fixed-length representations for arbitrarily-sized regions of the large FoV image. Specifically, an RoI projection can be performed to project a region of interest, such as one identified by the first model, onto the input large FoV image to extract a corresponding portion ("projection") from each feature map produced by the set of convolutional layers 802. The set of portions of the feature maps can then be subjected to the RoI pooling layer 804. An example RoI pooling layer is a max pooling layer that converts a projection into a 7-pixel by 7-pixel feature map.

Finally, the CNN can comprise a full-connected layer 806 to generate a final classification using the corresponding set of 7-pixel by 7-pixel feature maps. The full-connected layer can include the softmax function, which produces a probability of class membership for each of the classes, or in this case a probability of infection for each of the diseases or a probability of no infection.

In some embodiments, the second model can be built using any CNN module or library known to someone skilled in the art. For example, the ResNet50 model of the Keras library compatible with Python 2.7-3.5 can be utilized, with include_top set to True, max set to True, and classes set to 5. The five classes would correspond to background, gray leaf spot (GLS), Goss's Wilt (GW), NLB, and healthy leaf.

In some embodiments, to achieve scale invariance, the second model, such as a CNN, can be trained with single-size training or multi-size training. In other embodiments, the second model can include one or more other classification methods known to someone skilled in the art, such as linear regression, a Markov chain, or a recurrent neural network.

3.2 Image Scaling and Region Selection

In some embodiments, given a large FoV image, the server 170 is programmed to resize the given image at different scales to generate an image pyramid, so that a fixed-size sliding window can be used to find a leaf of an arbitrary size. The size of the sliding window would be the expected size of each of the second set of training images. Any content scaling method known to someone skilled in the art can be used, such as nearest-neighbor scaling or Lanczos resampling.

Figure 9:
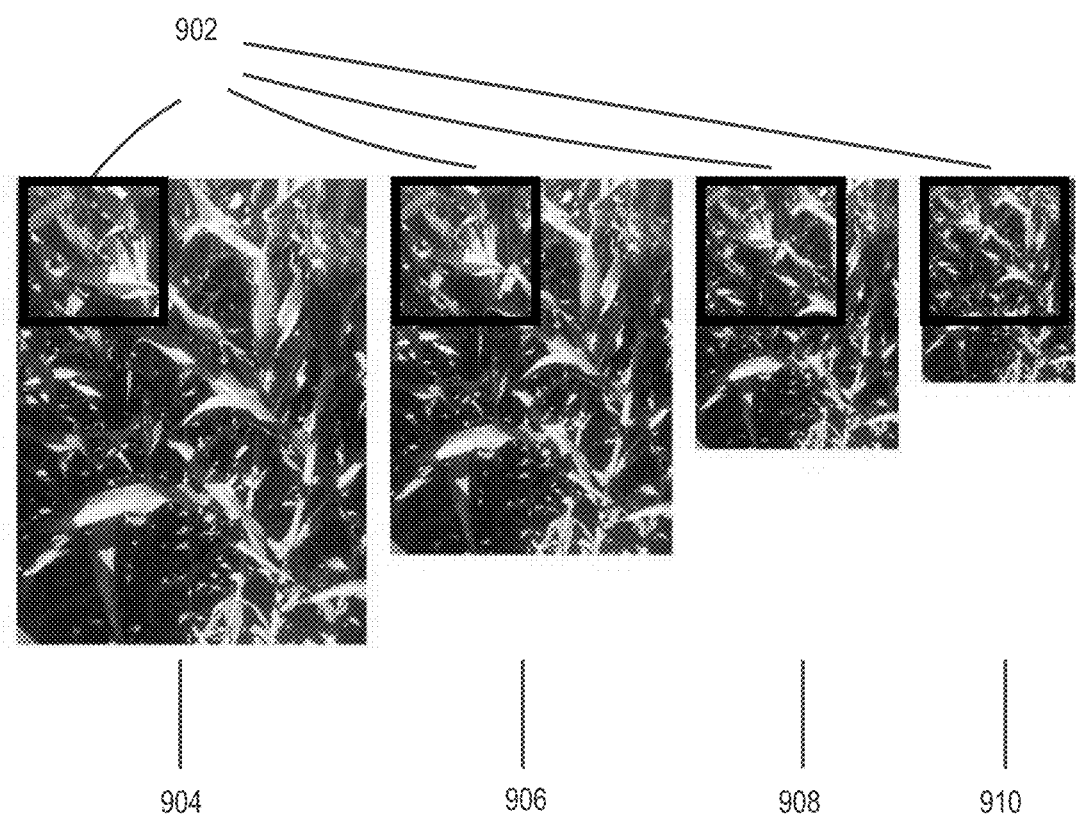
FIG. 9 illustrates an example scaling process to generate an image pyramid.

FIG. 9 illustrates an example scaling process to generate an image pyramid.

As one example, an original large FoV image may be sized 1,600 pixels by 1,200 pixels, and the images 904, 906, 908, and 910 may represent resized images at successively smaller scales, corresponding to sizes of 900 pixels by 800 pixels, 800 pixels by 600 pixels, 560 pixels by 420 pixels, and 400 pixels by 300 pixels, respectively. The smallest resized image 910 would still be larger than the size of a sliding window 902, which is sized 224 pixels by 224 pixels. As the resized images get smaller, the scaling method is expected to retain main features of the original image even if more information is lost. Therefore, as the image becomes smaller, the same sliding window 902 would correspond to a bigger region in the original image ideally with more or less the same features. Accordingly, at successively smaller scales, the sliding window 902 corresponds to a region in the original image that captures more and more leaves. For an image of a specific size, when the size of the field of view is large, the image might capture many leaves and each leaf could be represented in only a small area, and thus a large scale would be sufficient for a sliding window 902 to correspond to a region capturing a single leaf.

Similarly, when the size of the field of view is small, the image might capture few leaves and each leaf could be represented in a large area, and thus a small scale would be necessary for a sliding window 902 to correspond to a region capturing a single leaf. In general, any number of scales can be used, although a larger number of scales would mean a larger number of regions to consider.

In some embodiments, the server 170 is programmed to run the sliding window 902 through each resized image and execute the first model discussed above on the corresponding region to identify a candidate region likely to capture an intended target, such as a single leaf. Specifically, for each corresponding region, the server 170 is programmed to compute the HOG feature vector. The computation can be performed using any HOG module or library known to someone skilled in the art. For example, the HOGDescriptor function in the OpenCV library (version 3.3) can be used to compute the HOG feature vector with win_size set to Size(224,224), block_size set to Size(2,2), cell_size set to Size(32,32), and nbins set to 9. The server 170 is further programmed to execute the SVM on the HOG feature vector to determine whether the corresponding region can be classified as a candidate region likely to capture an intended target.

Figure 10:
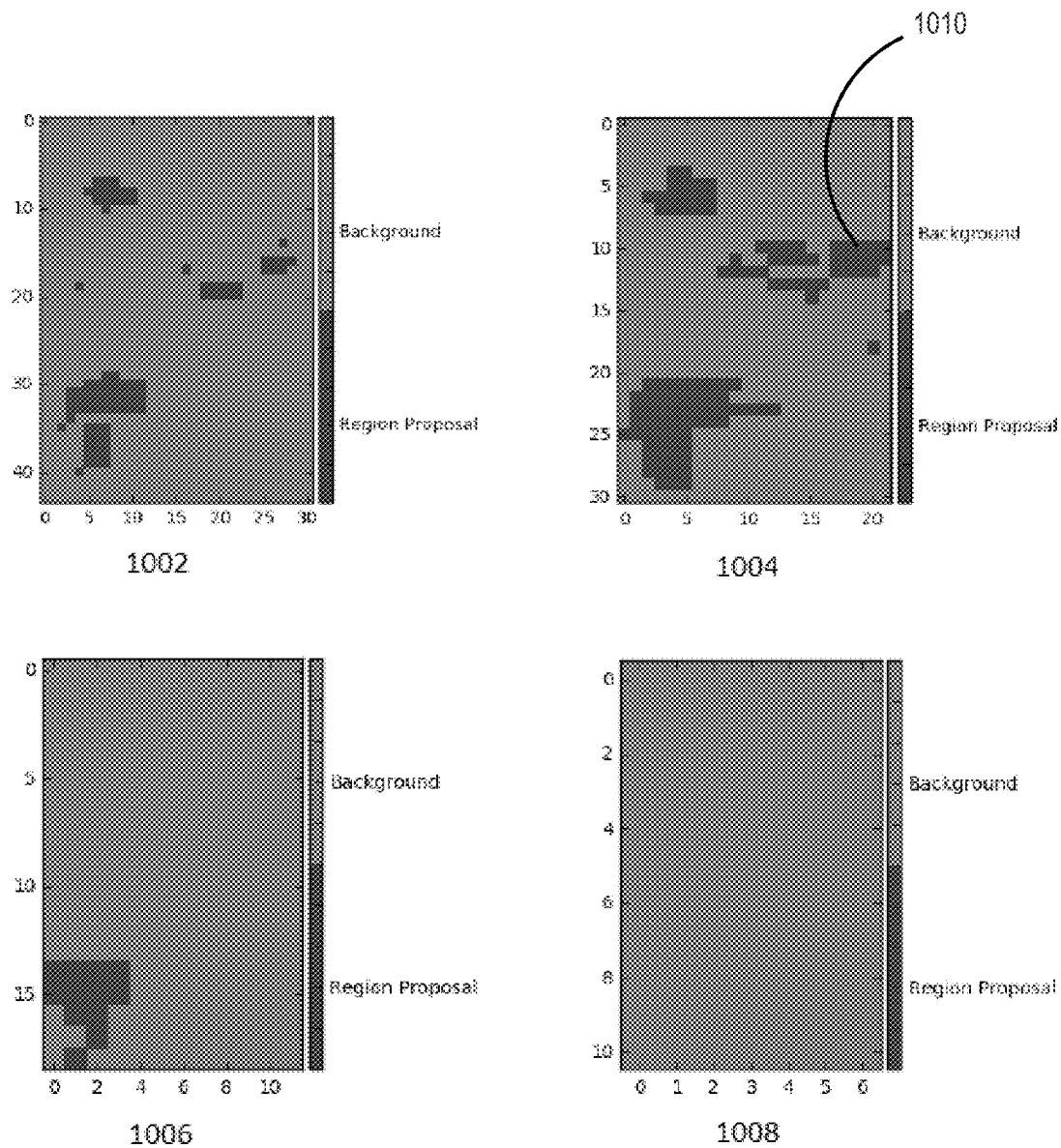
FIG. 10 illustrates an example result of region selection from an image pyramid.

FIG. 10 illustrates an example result of region selection from an image pyramid. The charts 1002, 1004, 1006, and 1008 may represent the original and resized images noted above having sizes 1,600 pixels by 1,200 pixels, 900 pixels by 800 pixels, 800 pixels by 600 pixels, and 560 pixels by 420 pixels, respectively. The x-axis and the y-axis of each chart indicates the dimension of the image in units of 40 pixels, although each chart is shown in the same size to indicate how the resized image maps back to the original image. The candidate regions are shown as dark areas in these charts, such as the drank region 1010. As can be seen from the charts 1002, 1004, and 1006, different candidate regions can be identified when the original image is resized at different scales. For example, the dark region 1010 appears clearly in the chart 1004 but only partially in the chart 1002 and not at all in the charts 1006 and 1008. In addition, the small number of candidate regions identified for smaller scales, as shown in the charts 1006 and 1008, is consistent with the large field of view associated with the original image.

3.3 Image Feature Computation

In some embodiments, the server 170 is programmed to execute the second model on the input large FoV image to initially compute features for the image to be used for determining whether the image captures any infected target, such as an infected leaf. Specifically, the server 170 is configured to execute the set of convolutional layers of the CNN on the large FoV image. The CNN is generally capable of extracting features of the target at different scales. Executing the set of convolutional layers on the large FoV image once is clearly more efficient than executing the set of convolutional layers additionally on the different resized images. Therefore, it is desirable to feed the large FoV image to the CNN, let different regions of the image be evaluated through convolution operations, but trim down the feature maps to focus on the candidate regions identified by the first model for the RoI pooling layer and the full-connected layer.

3.4 Image Region Classification and Mapping

In some embodiments, when the second model is the CNN, the server 170 is programmed to perform RoI projection, as noted above. Specifically, the server 170 is configured to take each candidate region identified by the first model, map it to the input large FoV image to obtained a mapped region, and extract a corresponding portion ("projected feature map") from each of the feature maps produced by the set of convolutional layers of the CNN. An example of this mapping procedure can be found in the article by He at all, arXiv:1406.4729v4 [cs.CV] (2015).

In some embodiments, the server 170 is programmed to execute the RoI pooling layer on each of the projected feature map corresponding to a candidate region identified by the first model. Since the RoI pooling layer is designed to work on a reasonably-sized region to produce a meaningful fixed-sized representation, it is desirable to send select regions of the feature maps output by the set of convolutional layers to the RoI pooling layer. Executing the RoI pooling layer on the projected feature maps corresponding to selected regions of the large FoV image is clearly more efficient than executing the RoI pooling layer on all possible portions of the feature maps corresponding to all possible sliding-window regions of the large FoV image. Therefore, the combination of executing the set of convolutional layers on the large FoV image and executing the RoI pooling layer on the projected feature maps achieves optimal execution efficiency.

In some embodiments, the initial image scaling to generate an image pyramid can be replaced by setting the RoI pooling layer up as a spatial pyramid pooling layer. In this case, the server 170 can be configured to identify different sets of spatial bins from each feature map corresponding to different scales. The server 170 can be further configured to feed each of the spatial bins as a region of interest to the RoI pooling layer or utilize the first model to filter some of the spatial bins.

In some embodiment, the server 170 is configured to execute the full-connected layer on each set of projected feature maps outputted by the RoI pooling layer for each mapped region of the large FoV image to determine whether the mapped region can be classified as an intermediary region likely to capture an infected target for each of the diseases. The fully-connected layer can produce, for each mapped region, a probability of infection for each of the disease classes or a probability of no infection. The server 170 can be further configured to classify a mapped region as an intermediary region based on a predetermined criterion related to a probability of infection, such when a probability of infection exceeds a certain threshold or is among the highest 5%.

Figure 11:
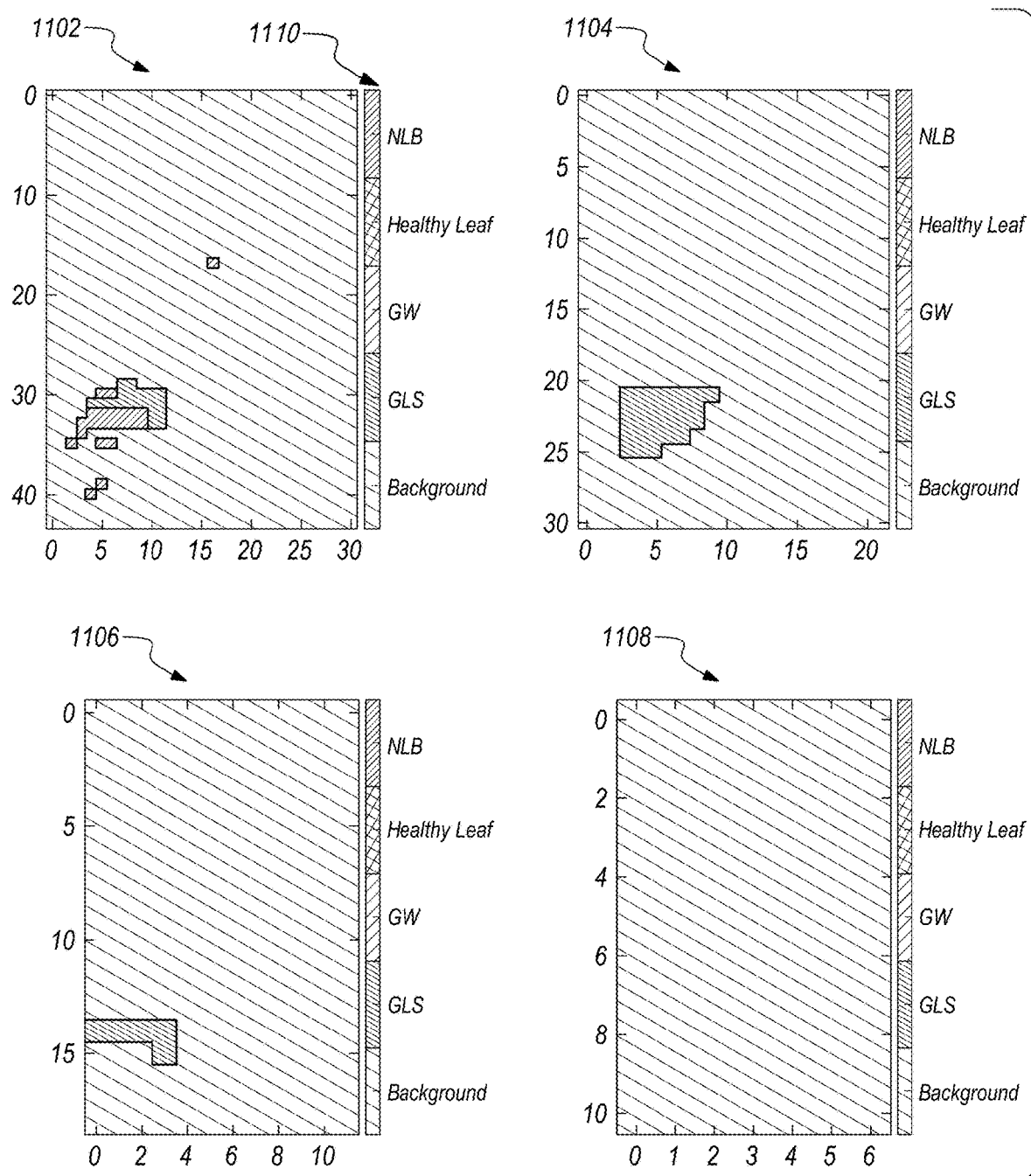
FIG. 11 illustrates an example output of a second model for identifying regions likely to capture infected targets.

FIG. 11 illustrates an example output of a second model for identifying regions likely to capture infected targets. The charts 1102, 1104, 1106, and 1108 may represent the original and resized images noted above having sizes 1,600 pixels by 1,200 pixels, 900 pixels by 800 pixels, 800 pixels by 600 pixels, and 560 pixels by 420 pixels, respectively. The x-axis and the y-axis of each chart indicates the dimension of the image in units of 40 pixels, although each chart is shown in the same size to indicate how the resized image maps back to the original image. The candidate regions (having mapped regions) that have been deemed likely to capture infected leaves are shown in different shading patterns corresponding to different diseases in these charts, as indicated by the legend 1010 in each of the charts. As can be seen from the charts 1102, 1104, and 1106, the same infected leaf may be identified from images at different scales. It can also be seen from the chart 1102 that same leaf, different portions of the same leaf, or nearby leaves may be determined to be infected with different diseases.

In some embodiments, the server 170 is programmed to condense the set of intermediary regions identified by the second model through non maximum suppression. Since a sliding window is used for the first model to identify candidate regions, many of the candidate regions identified by the first model, many of the mapped regions identified by the second model, and many of the intermediary regions may overlap. Therefore, the server 170 is configured to systematically eliminate overlapping regions from consideration as final regions. Specifically, out of the intermediary regions, the one having a highest probability of infection and an associated disease is first chosen. Any region that overlaps with the chosen intermediary region by more than a predetermined threshold, such as 40% of either of the overlapping regions, can then be removed from consideration as a final region. This process can then be repeated on the remaining intermediary regions for a number of times until a predetermined criterion is satisfied, such as more than a certain number of iterations have been performed or fewer than a certain number of intermediary regions remain. Alternatively, the server 170 can be configured to divide the set of intermediary regions into clusters of overlapping regions and select one region from each of the clusters simultaneously or in no particular order.

Figure 12:
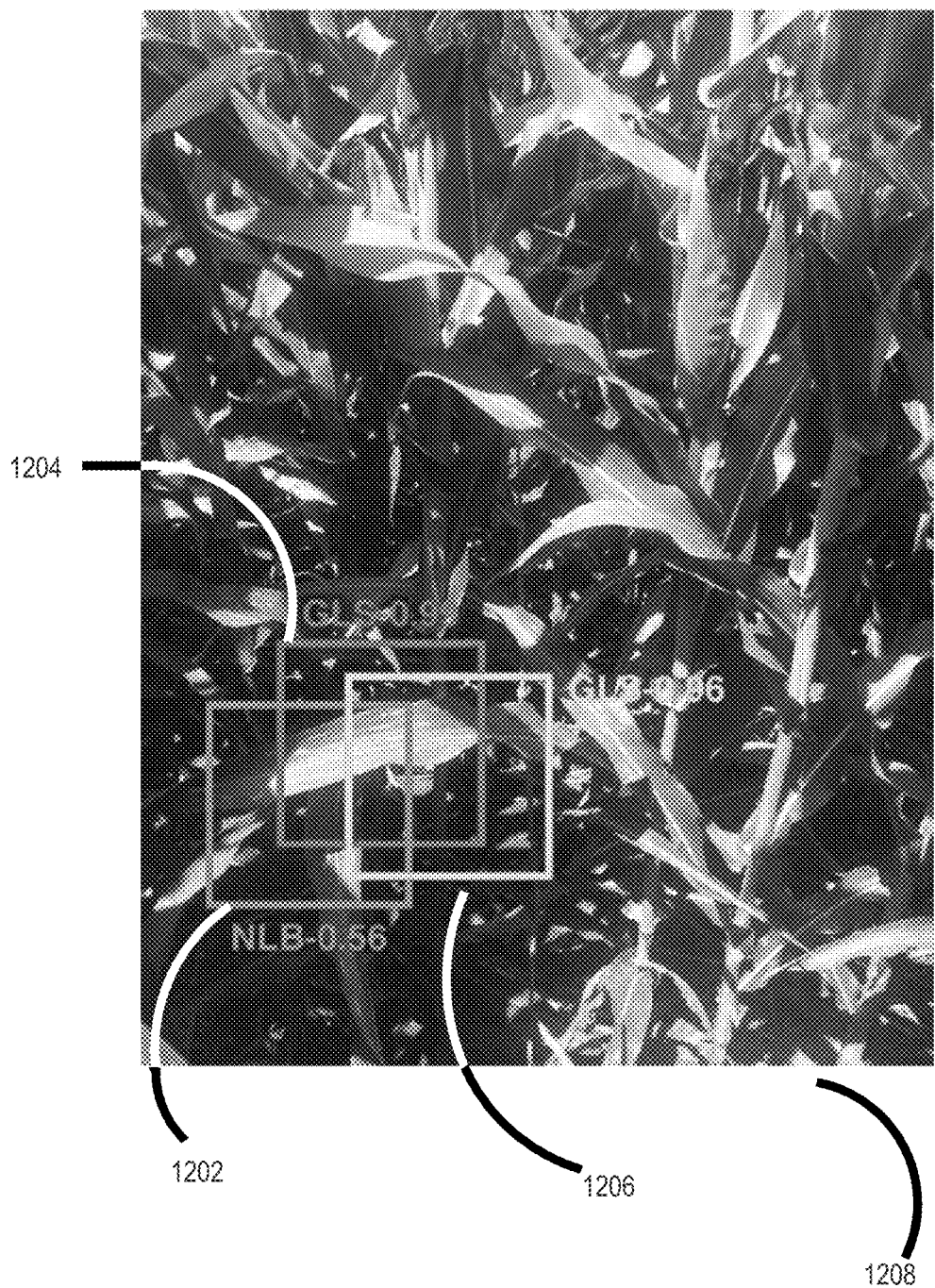
FIG. 12 illustrates an example application of non maximum suppression.

FIG. 12 illustrates an example application of non maximum suppression. In a given large FoV image 1208, some candidate regions of the resized images, including those corresponding to the mapped regions 1202, 1204, and 1206, have been determined as likely to capture infected leaves. Since these regions overlap substantially, they may capture the same infected leaf. Therefore, the one associated with a highest probability of infection, namely the region 1204 associated with a probability of 99%, would be selected as a final region. The server 170 can report that the leaf captured in the region 1204 may be infected by GLS with a 99% probability. After removing the mapped regions 1202, 1204, and 1206 from further consideration, if any mapped region remains, the process can be repeated.

In some embodiments, the server 170 is programmed to transmit data related to the final regions to a display device, a client device, or a remote server over a communication network. The data can include, for each final region, the position within the input large FoV image, the disease likely infected, or the probability of infection.

3.5 Example Programmable Processes

Figure 13:
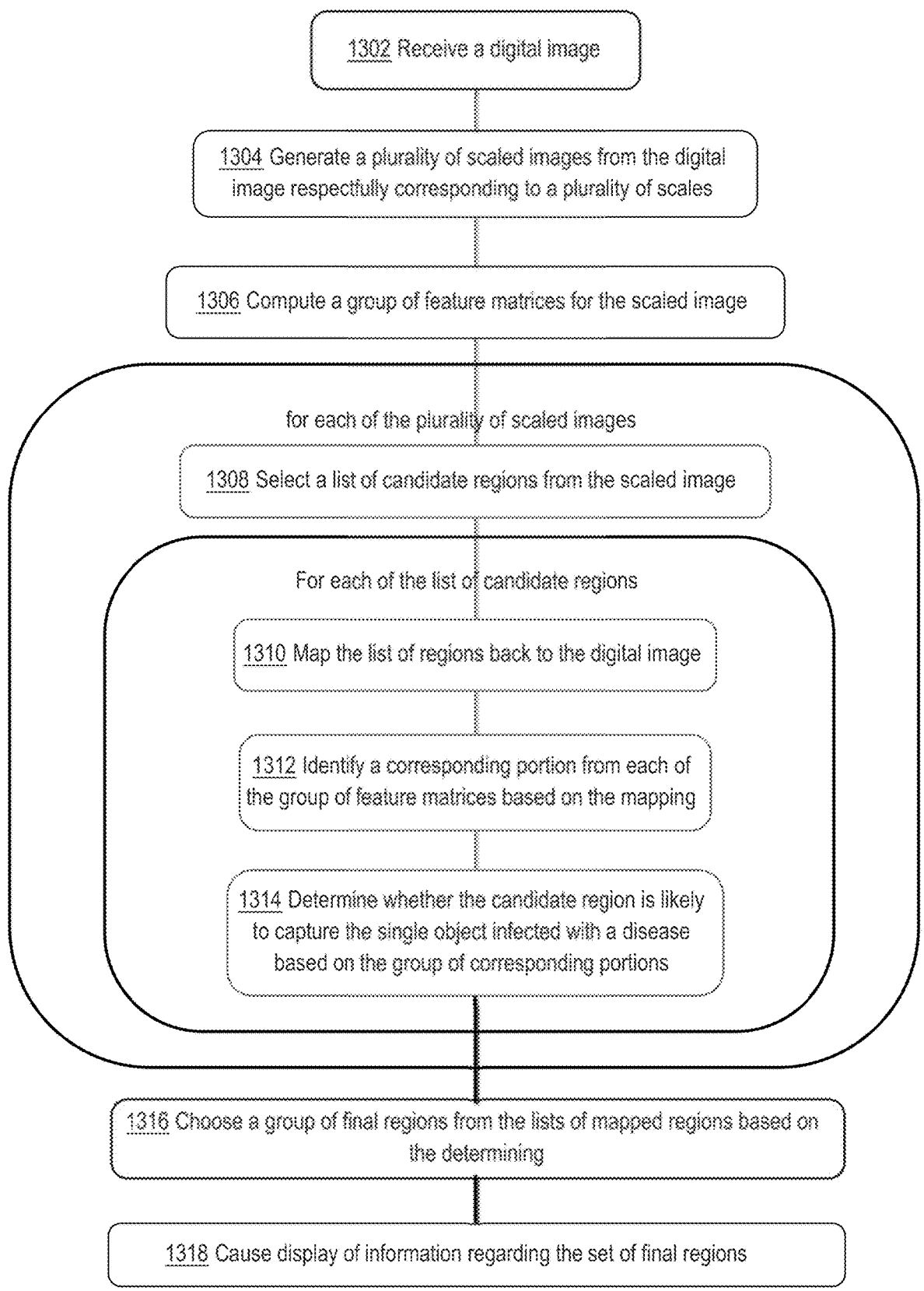
FIG. 13 illustrates an example process of identifying infected targets from a large FoV image.

FIG. 13 illustrates an example process of identifying infected targets from a large FoV image.

In some embodiments, the server 170 is programmed to build a first model for determining whether a region is likely to capture a single target, such as a leaf. The first model can include or communicate with a HOG module that computes a HOG feature vector for a region. The first model can also include an SVM that classifies a region into one of several classes based on the feature vector, such as a class of single leaves and a class of no leaves or multiple leaves, which can lead to the identification of a candidate region likely to capture a single target.

In some embodiments, the server 170 is programmed to also build a second model for determining whether a large FoV image is likely to capture infected targets, such as infected leaves, or whether specific regions of the FoV image is likely to capture individual infected targets. The second model can include a CNN that comprises a set of convolutional layers, a RoI pooling layer, and a fully-connected layer. The set of convolutional layers functions as the HOG module of the first model in computing feature values for an input image, which can be represented as be vectors, maps, or matrices. However, the set of convolutional layers can extract features of the single object at different scales directly from the large FoV image. The RoI pooling layer can process a set of projected feature maps produced by the set of convolutional layers for each candidate region identified by the first model into the feature maps. Finally, the fully-connected layer can classify each candidate region or the corresponding mapped region in the large FoV image into each of several classes, such as a class of a leaf infected with a certain disease and a class of a healthy leaf, for a certain probability based on the output of the RoI pooling layer. The output of the fully-connected layer can further lead to the identification of an intermediary region likely to capture a single target infected with a certain disease.

In some embodiments, with the first and the second models in place, in step 1302, the server 170 is configured to receive a digital image capturing multiple objects, such as a large FoV photo of a corn field. In step 1304, the server 170 is programmed to generate a plurality of scaled images of the received digital image. The number or dimensions of the scales can depend on the possible sizes of the field of view, the amount of available computational resources, or other factors.

In some embodiments, the server 170 is programmed to execute the first model on each of the scaled images to identify candidate regions of the received digital image, each likely to capture a single object, and execute the second model to ultimately identify intermediary regions from the candidate regions, each likely to capture the single object infected with a certain disease, such as a corn leaf infected with NLB. When the second model is a CNN, using the set of convolutional layers to obtain feature maps separately for different candidate regions can be time-consuming. In step 1306, however, the server 170 is configured to use the set of convolutional layers once to extract features of the single object at different scales directly from the received digital image.

In some embodiments, in step 1308, the server 170 is configured to execute the first model on each of the scaled images to identify the candidate regions, as noted above. This step can also be performed before step 1306. The server 170 is programmed to next execute the rest of the second model for each of the candidate regions to identify the intermediary regions. Specifically, in step 1310 and step 1312, the server 170 is programmed to map the candidate region identified from a scaled image back to the original, received digital image to obtain a mapped region and also to each of the group of feature maps produced by the set of convolutional layers to obtain a group of projected feature maps. In step 1314, the server 170 is programmed to feed only the group of projected feature maps, which are clearly smaller than the feature maps, to the RoI layer, and send the output of the RoI layer to the fully-connected layer to determine whether the candidate region captures a single target infected with one of the predetermined diseases for a certain probability of infection. The server 170 is further configured to determine whether the candidate region can be an intermediary region likely to capture the single target infected with a certain disease based on the associated probabilities of infection.

In some embodiments, in step 1316, the server 170 is programmed to clean up the list of intermediary regions to obtain the final regions. The clean-up can consolidate duplicate or highly overlapping regions or further filter the regions based on the associated probabilities of infection. The elimination of overlapping regions can be performed through non maximum suppression. Finally, in step 1318, the server 170 is programmed to transmit data regarding the final regions to a display device, a client device, or a remote server. The data can include, for each final region, the position within the received digital image, the associated probability of infection, the infected disease, or other information.

What is claimed is:

1. A computer-implemented method of detecting infected objects from large field-of-view images, comprising:
   receiving, by a processor, a first set of training images,
      at least a certain image of the first set of training images capturing an object of a certain type in more than half of a total area of the certain image;
   building, by the processor, a first digital model based on the first set of training images,
      the first digital model configured to receive a list of feature vectors of a first input image and produce a determination of whether the first input image captures an object of the certain type;
   receiving a second set of training images,
      for each of a plurality of classes, at least a specific image of the second set of training images capturing an object of the certain type that is associated with the class in more than half of a total area of the specific image;
   augmenting, for a plurality of scales, the second set of training images with copies of a group of the second set of training images resized at the plurality of scales to generate an augmented set of training images including the second set of training images;
   creating a second digital model based on the augmented set of training images,
      the second digital model configured to receive a second input image capturing a plurality of objects of the certain type and produce a determination of whether a region of the second input image captures an object of the certain type associated with any of the plurality of classes;
   receiving a third input image capturing multiple objects of the certain type;
   identifying a plurality of regions from the third input image using the first digital model;
   computing a group of feature matrices for the third input image using the second digital model;
   mapping a candidate region of the plurality of regions back to the third input image to obtain a mapped region;
   identifying a corresponding portion from each of the group of feature matrices based on the mapping; and
   determining whether the candidate region is likely to capture an object of the certain type associated with one of the plurality of classes using the second digital model;
   causing display of information related to the determining.

2. The computer-implemented method of claim 1, wherein the first set of training images comprises:
   a first subset of images labeled as positive samples, where, for each specific positive image of the first subset of images, an object of the certain type is captured in more than half of a total area of the specific positive image; and
   a second subset of images labeled as negative samples, where, for each specific negative image of the second subset of images, two or more objects are captured in the specific negative image, one object is captured in less than half of the total area of the specific negative image, or no objects are captured in the specific negative image.

3. The computer-implemented method of claim 1, wherein the first digital model implements a support vector machine (SVM) model configured to determine whether the first input image captures the object of the certain type.

4. The computer-implemented method of claim 1, wherein the list of feature vectors of the first input image comprise a histogram of oriented gradients (HOG) value for the first input image.

5. The computer-implemented method of claim 1, wherein the second digital model implements a convolutional neural network comprising:
   a set of convolutional layers configured to generate feature matrices for the second input image; and
   a fully-connected layer configured to determine, based on the feature matrices, whether the region of the second input image captures the object of the certain type associated with any of the plurality of classes.

6. The computer-implemented method of claim 5, wherein the convolutional neural network further comprises a region-of-interest pooling layer configured to generate fixed-length representations of regions of the second input image; and
   wherein output data from the region-of-interest pooling layer becomes input data to the fully-connected layer.

7. The computer-implemented method of claim 1, further comprising, upon receiving the second set of training images, trimming each training image, in the second set of training images, to a fixed size.

8. The computer-implemented method of claim 1, further comprising:
    generating an additional set of training images using at least a subset of the second set of training images as input for a generative adversarial network; and
    adding the additional set of training images to the augmented set of training images.

9. The computer-implemented method of claim 1, wherein augmenting the second set of training images comprises:
    creating an additional set of training images having copies of the second set of training images;
    modifying at least a subset of the additional set of training images by performing at least one of: image rotation followed by image shearing, image scaling, and image enlargement followed by image chopping; and
    generating, after the modifying, the augmented set of training images that include the additional set of training images.

10. The computer-implemented method of claim 1, wherein identifying the plurality of regions from the third input image comprises:
    generating a plurality of scaled input images from the third input image respectfully corresponding to the plurality of scales; and
    identifying the plurality of regions, from the plurality of scaled input images, each likely to capture an object of the certain type.

11. The computer-implemented method of claim 1, wherein the information indicating, for the candidate region, a position of the candidate region within the third input image and the certain type of the object.

12. A non-transitory computer-readable storage medium storing one or more instructions which, when executed by one or more processors, cause the one or more processors to perform a method of detecting infected objects from large field-of-view images, the method comprising:
    receiving, by a processor, a first set of training images,
        at least a certain image of the first set of training images capturing an object of a certain type in more than half of a total area of the certain image;
    building, by the processor, a first digital model based on the first set of training images,
        the first digital model configured to receive a list of feature vectors of a first input image and produce a determination of whether the first input image captures an object of the certain type;
    receiving a second set of training images,
        for each of a plurality of classes, at least a specific image of the second set of training images capturing an object of the certain type that is associated with the class in more than half of a total area of the specific image;
    augmenting, for a plurality of scales, the second set of training images with copies of a group of the second set of training images resized at the plurality of scales to generate an augmented set of training images including the second set of training images;
    creating a second digital model based on the augmented set of training images,
        the second digital model configured to receive a second input image capturing a plurality of objects of the certain type and produce a determination of whether a region of the second input image captures an object of the certain type associated with any of the plurality of classes;
    receiving a third input image capturing multiple objects of the certain type;
    identifying a plurality of regions from the third input image using the first digital model;
    computing a group of feature matrices for the third input image using the second digital model;
    mapping a candidate region of the plurality of regions back to the third input image to obtain a mapped region;
    identifying a corresponding portion from each of the group of feature matrices based on the mapping; and
    determining whether the candidate region is likely to capture an object of the certain type associated with one of the plurality of classes using the second digital model;
    causing display of information related to the determining.

13. The non-transitory computer-readable storage medium of claim 12, wherein the first set of training images comprises:
    a first subset of images labeled as positive samples, where, for each specific positive image of the first subset of images, an object of the certain type is captured in more than half of a total area of the specific positive image; and
    a second subset of images labeled as negative samples, where, for each specific negative image of the second subset of images, two or more objects are captured in the specific negative image, one object is captured in less than half of the total area of the specific negative image, or no objects are captured in the specific negative image.

14. The non-transitory computer-readable storage medium of claim 12, wherein the first digital model implements a support vector machine (SVM) model configured to determine whether the first input image captures the object of the certain type.

15. The non-transitory computer-readable storage medium of claim 12, wherein the list of feature vectors of the first input image comprise a histogram of oriented gradients (HOG) value for the first input image.

16. The non-transitory computer-readable storage medium of claim 12, wherein the second digital model implements a convolutional neural network comprising:
    a set of convolutional layers configured to generate feature matrices for the second input image; and
    a fully-connected layer configured to determine, based on the feature matrices, whether the region of the second input image captures the object of the certain type associated with any of the plurality of classes.

17. The non-transitory computer-readable storage medium of claim 16, wherein the convolutional neural network further comprises a region-of-interest pooling layer configured to generate fixed-length representations of regions of the second input image; and
    wherein output data from the region-of-interest pooling layer becomes input data to the fully-connected layer.

18. The non-transitory computer-readable storage medium of claim 12, wherein the one or more instructions, when executed by the one or more processors, further cause, upon receiving the second set of training images, trimming each training image, in the second set of training images, to a fixed size.

19. The non-transitory computer-readable storage medium of claim 12, wherein the one or more instructions, when executed by the one or more processors, further cause:
    generating an additional set of training images using at least a subset of the second set of training images as input for a generative adversarial network; and adding the additional set of training images to the augmented set of training images.

20. The non-transitory computer-readable storage medium of claim 12, wherein augmenting the second set of training images comprises:
creating an additional set of training images having copies of the second set of training images;
modifying at least a subset of the additional set of training images by performing at least one of: image rotation followed by image shearing, image scaling, and image enlargement followed by image chopping; and
generating, after the modifying, the augmented set of training images that include the additional set of training images.

* * * * *